(12) United States Patent
Gerlach et al.

(10) Patent No.: US 7,211,679 B2
(45) Date of Patent: *May 1, 2007

(54) PERFLUOROETHER ACYL OLIGOTHIOPHENE COMPOUNDS

(75) Inventors: Christopher P. Gerlach, St. Paul, MN (US); David A. Ender, New Richmond, WI (US); Dennis E. Vogel, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 220 days.

This patent is subject to a terminal disclaimer.

(21) Appl. No.: 11/076,268

(22) Filed: Mar. 9, 2005

(65) Prior Publication Data

US 2006/0205172 A1 Sep. 14, 2006

(51) Int. Cl.
*H01B 1/12* (2006.01)
*C07D 333/04* (2006.01)
*C07D 333/28* (2006.01)

(52) U.S. Cl. .................. 549/71; 549/73; 252/500; 528/377

(58) Field of Classification Search ............... 252/500; 528/377, 280; 549/70, 71, 73
See application file for complete search history.

(56) References Cited

U.S. PATENT DOCUMENTS

| 3,242,218 A | 3/1966 | Miller |
| 3,250,808 A | 5/1966 | Moore, Jr. et al. |
| 3,274,239 A | 9/1966 | Selman |
| 3,293,306 A | 12/1966 | Le Bleu et al. |
| 3,322,826 A | 5/1967 | Moore |
| 3,536,710 A | 10/1970 | Bartlett |
| 3,544,537 A | 12/1970 | Brace et al. |
| 3,553,179 A | 1/1971 | Bartlett |
| 3,647,712 A | 3/1972 | Lucid |
| 3,810,874 A | 5/1974 | Mitsch et al. |
| 3,864,318 A | 2/1975 | Caporiccio et al. |
| 4,321,404 A | 3/1982 | Williams et al. |
| 4,472,480 A | 9/1984 | Olson |
| 4,567,073 A | 1/1986 | Larson et al. |
| 4,647,413 A | 3/1987 | Savu |
| 4,749,526 A | 6/1988 | Flynn |
| 4,818,801 A | 4/1989 | Rice et al. |
| 4,830,910 A | 5/1989 | Larson |

(Continued)

FOREIGN PATENT DOCUMENTS

JP 2002-322173 11/2002

OTHER PUBLICATIONS

Facchetti et al., "Electron-Transporting Thiophene-Based Semiconductors Exhibiting Very High Field Effect Mobilities", Mat. Res. Soc. Symp. Proc., (2004), pp. I12.2.1-I12.2.6, vol. 814, Materials Research Society.

(Continued)

*Primary Examiner*—Mark Kopec
(74) *Attorney, Agent, or Firm*—Kent S. Kokko; John M. Bronk

(57) ABSTRACT

Semiconductor devices are described that include a semiconductor layer that comprises a perfluoroether acyl oligothiophene compound, preferably an α,ω-bis-perfluoroether acyl oligothiophene compound. Additionally, methods of making semiconductor devices are described that include depositing a semiconductor layer that contains a perfluoroether acyl oligothiophene compound, preferably an α,ω-bis (2-perfluoroether acyl oligothiophene compound.

17 Claims, 3 Drawing Sheets

U.S. PATENT DOCUMENTS

| | | | |
|---|---|---|---|
| 5,034,049 | A * | 7/1991 | Kober et al. ............... 504/289 |
| 5,306,758 | A | 4/1994 | Pellerite |
| 5,347,144 | A | 9/1994 | Garnier et al. |
| 5,362,919 | A | 11/1994 | Costello et al. |
| 5,578,278 | A | 11/1996 | Fall et al. |
| 5,705,826 | A | 1/1998 | Aratani et al. |
| 5,854,139 | A | 12/1998 | Aratani et al. |
| 6,127,496 | A | 10/2000 | Tonelli et al. |
| 6,433,359 | B1 | 8/2002 | Kelley et al. |
| 6,585,914 | B2 | 7/2003 | Marks et al. |
| 6,608,323 | B2 | 8/2003 | Marks et al. |
| 6,617,609 | B2 | 9/2003 | Kelley et al. |
| 6,821,348 | B2 | 11/2004 | Baude et al. |
| 6,897,164 | B2 | 5/2005 | Baude et al. |
| 6,906,534 | B2 | 6/2005 | Hoisington et al. |
| 2003/0102471 | A1 | 6/2003 | Kelley et al. |
| 2003/0151118 | A1 | 8/2003 | Baude et al. |
| 2004/0222412 | A1 | 11/2004 | Bai et al. |
| 2006/0186401 | A1 * | 8/2006 | Marks et al. ............... 257/40 |

OTHER PUBLICATIONS

Portnoy et al., "Synthesis of 2-Heptafluorobutyryl-thiophene", J. Org. Chem., Communications, (Dec. 1957), pp. 1752-1753, vol. 22.

Portnoy et al., "Flourinated Acylthiophenes. Preparation of 5,5'-Diheptafluorobutyryl-2,2'-bithiophene via a Grignard Coupling Reaction", J. Org. Chem., Notes, (Jan. 1967), pp. 233-234, vol. 32.

Linderman et al., Addition of Organocuprates to Acetylenic Di- and Trifluoromethyl Ketones. Regiospecific Synthesis of β, β-Disubstituted Unsaturated Fluoro Ketones, J. Org. Chem., (1988), pp. 6013-6022, vol. 53, No. 26.

Wu et al., "Room Temperature Stable 3-Lithiothiophene: A Facile Synthesis of 3-Functional Thiophenes", Tetrahedron Letters, (1994), pp. 3673-3674, vol. 35, No. 22, Elsevier Science Ltd.

Wei et al., "Synthesis and Electronic Properties of Aldehyde End-Capped Thiophene Oligomers and Other α,ω-Substituted Sexithiophenes", Chem. Mater., (1996), pp. 2659-2666, vol. 8, No. 11, American Chemical Society.

Katz et al., "Synthesis, Solubility, and Field-Effect Mobility of Elongated and Oxa-Substituted α,ω-Dialkyl Thiophene Oligomers. Extension of "Polar Intermediate" Synthetic Strategy and Solution Deposition on Transistor Substrates", Chem. Mater. (1998), pp. 633-638, vol. 10, No. 2, American Chemical Society.

Yamaguchi et al., "A Convenient Synthesis of Alkynyl Ketones from Esters", Synthesis, Communications, (May 1986), pp. 421-422.

Sze, Physics of Semiconductor Devices, (1981), 2nd Edition, John Wiley & Sons, Inc., New York, NY, cover page & contents page.

Paquette, et al., Organic Reactions, (1997), vol. 50, John Wiley & Sons, Inc., New York, NY, cover page only.

Savu, "Fluorinated Higher Carboxylic Acids", Kirk-Othmer Encyclopedia of Chemical Technology, Fluorine Compounds, Organic (Higher Acids), (1994), pp. 551-558, vol. 11, 4th Edition.

Sheraw et al., "Spin-On Polymer Gate Dielectric for High Performance Organic Thin Film Transistors", Materials Research Society Symposium Proceedings, (2000), pp. 403-408, vol. 558, Materials Research Society, Warrendale, PA.

Van Zant, "Microchip Fabrication", (2004) 4th Edition, McGraw-Hill, NY, cover page only.

Facchetti, A., et al., "Building Blocks for n-Type Molecular and Polymeric Electronics. Perfluoroalky-versus Alkyl-Functionalized Oligothiophenes (nT; n=2-6). Systematics of Thin Film Microstructure, Semiconductor Performance, and Modeling of Majority Charge Injection in Field-Effect Transistors," Journal of the American Chemistry Society, vol. 126, No. 42, (2004) pp. 13859-13874.

Facchetti, A., et al, "Building Blocks for N-Type Molecular and Polymeric Electronics. Perfluoroalkyl-versus Alkyl-Functionalized Oligothiophenes (nTs; n=2-6). Systematic Synthesis, Spectroschopy, Electrochemistry, and Solid-State Organization," Journal of the American Chemistry Society, vol. 126, No. 41, (2004) pp. 13480-13501.

Facchetti, A., et al., "n-Type Building Blocks for Organic Electronics: A Homologous Family of Fluorocarbon-Substituted Thiophene Oligomers with High Carrier Mobility," Advanced Materials, vol. 15, No. 1, (2003) pp. 33-38.

Facchetti, A. et al., "Synthesis and Characterization of Diperfluorooctyl-Substituted Phenylene-Thiophene Oligomers as n-Type Semiconductors. Molecular Structure-Film Microstructure-Mobility Relationships, Organic Field-Effect Transistors, and Transistor Nonvolatile Memory Elements" American Chemistry Society, vol. 16, No. 23, (2003) pp. 4715-4727.

Yoon, M-H., et al., "Organic Thin-Film Transistors Based on Carbonyl-Functionalized Quaterthiophenes: High Mobility N-Channel Semiconductors and Ambipolar Transport," Journal of the American Chemistry Society, vol. 127, No. 5, (2005) pp. 1348-1349.

* cited by examiner

PERFLUOROETHER ACYL OLIGOTHIOPHENE COMPOUNDS

TECHNICAL FIELD

The present invention provides semiconductor devices and methods of making semiconductor devices that include a semiconductor layer that contains a perfluoroether acyl oligothiophene compound.

BACKGROUND

Traditionally, inorganic materials have dominated the semiconductor industry. For example, silicon arsenide and gallium arsenide have been used as semiconductor materials, silicon dioxide has been used as an insulator material, and metals such as aluminum and copper have been used as electrode materials. In recent years, however, there has been an increasing research effort aimed at using organic materials rather than the traditional inorganic materials in semiconductor devices. Among other benefits, the use of organic materials may enable lower cost manufacturing of electronic devices, may enable large area applications, and may enable the use of flexible circuit supports for display backplanes or integrated circuits.

A variety of organic semiconductor materials have been considered, the most common being fused aromatic ring compounds as exemplified by tetracene and pentacene, bis(acenyl)acetylene, and acene-thiophenes; oligomeric materials containing thiophene or fluorene units; and polymeric materials such as regioregular poly(3-alkylthiophene). At least some of these organic semiconductor materials have performance characteristics such as charge-carrier mobility, on/off current ratios, and sub-threshold voltages that are comparable or superior to those of amorphous silicon-based devices.

Thiophene chemistry and the chemical stability of the thiophene ring hold potential for use of thiophene materials in molecular-based electronics and photonics. In particular, α,α'-conjugated thiophene oligomers (nTs) and polymers (polythiophenes-PTs) have attracted great interest as semiconducting elements in organic thin-film transistors (TFTs). To be useful in such devices and related structures, the organic material must support a channel of holes or electrons (p- or n-type semiconductor, respectively) created by the gate electrode bias, which switches the device "on". Furthermore, the charge mobility of the material must be sufficiently large to increase the source-drain on-conduction by many orders of magnitude over the "off" state. The density of the charge carrier in the channel is modulated by voltage applied at the gate electrode U.S. Pat. No. 6,585,914 (Marks et al.) describe α,ω-diperfluoroalkylsexithiophene-evaporated films of which behave as n-type semiconductors, and can be used to fabricate thin film transistors with FET mobilities about 0.01 cm²/Vs.

SUMMARY

Novel perfluoroether acyl (oligo)thiophene compounds, including α,ωbis-perfluoroether acyl oligothiophene compounds are provided. Additionally, a novel method of preparing the compounds is provided. The compounds are useful, for example, as n-channel semiconductor layers in electronic devices, such as thin film transistors. There are a considerable number of problems and deficiencies associated with the prior art relating to useful organic n-type semiconductor compounds, compositions and/or materials. There is a demonstrated need for such materials, compositions, layers and/or composites for thin film deposition and related applications useful in conjunction with the fabrication of thin film transistors and related devices as can be incorporated into an integrated circuit. Accordingly, it is an object of the present invention to provide new and useful n-type organic materials, together with one or more methods of preparation.

Semiconductor devices and methods of making the semiconductor devices are provided. More specifically, the semiconductor devices include a semiconductor layer that contains at least one perfluoroether acyl oligothiophene compound, preferably at least one α,ω-bis-perfluoroether acyl oligothiophene compound.

The novel compounds may be represented by the formula

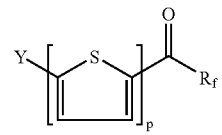

I wherein Y is a hydrogen atom, a halogen atom, an alkyl group, an aryl group or a perfluoroether acyl group, p is at least one, preferably at least two, and $R_f$ is a perfluoroether group.

Preferred compounds are those α,ωbis-perfluoroether acyl oligothiophene compounds of Formula II:

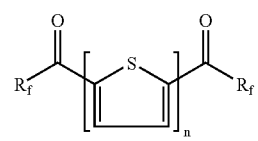

II wherein each $R_f$ is a perfluoroether group, and n is at least 1, preferably at least 2, more preferably 3 to 6. Using the conventional nomenclature, the successive thiophene rings are connected by a covalent bond, as indicated in Formulas I and II. In one aspect, semiconductor devices are provided that include a semiconductor layer that contains a α,ω-bis-perfluoroether acyl oligothiophene compound of Formulas I or II.

In another aspect, a method of preparing a semiconductor device is provided. The method involves preparing a semiconductor layer that contains a compound of Formula II. The semiconductor layer is often formed using a vapor deposition technique.

Some of the methods of preparing semiconductor devices are methods of preparing organic thin film transistors. One such method involves providing a gate electrode; depositing a gate dielectric layer on a surface of the gate electrode; preparing a semiconductor layer adjacent to a surface of the gate dielectric layer opposite the gate electrode; and positioning a source electrode and a drain electrode on a surface of the semiconductor layer that is opposite the gate dielectric layer. The source electrode and the drain electrode are separated from each other in an area on the surface of the semiconductor layer. The semiconductor layer contains a compound of Formulas I or II.

An additional method of preparing an organic thin film transistor involves providing a gate electrode; depositing a gate dielectric layer on a surface of the gate electrode; positioning a source electrode and a drain electrode adjacent to the gate dielectric layer opposite the gate electrode, wherein the source electrode and the drain electrode are separated by an area over the gate dielectric layer; and preparing a semiconductor layer on the source electrode, the drain electrode, and in the area between the source electrode and the drain electrode. The semiconductor layer includes a compound of Formulas I or II.

The above summary of the present invention is not intended to describe each disclosed embodiment or every implementation of the present invention. The Figures, Detailed Description, and Examples that follow more particularly exemplify these embodiments. While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

BRIEF DESCRIPTION OF THE DRAWINGS

The invention may be more completely understood in consideration of the following detailed description of various embodiments of the invention in connection with the accompanying drawings, in which.

DETAILED DESCRIPTION

Figure 1A:
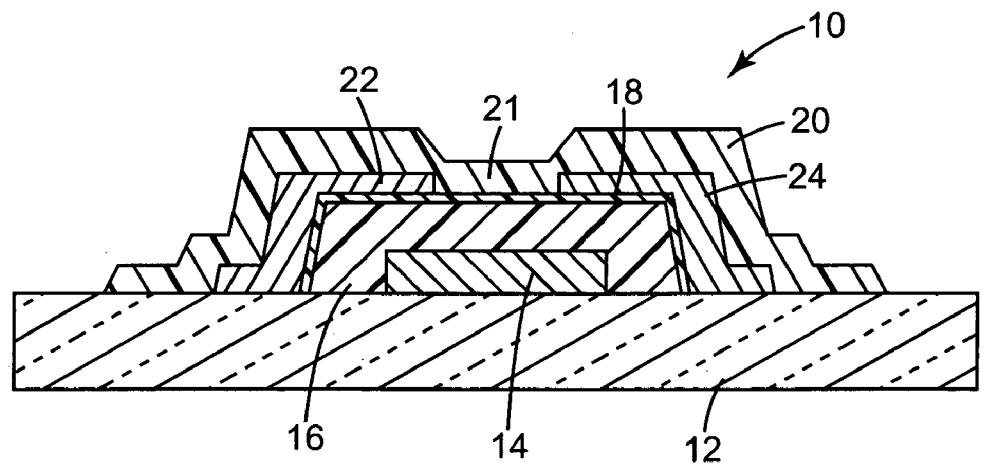
FIGS. 1a and b show cross-sectional representations of exemplary organic thin film transistors.

Novel perfluoroether acyl (oligo)thiophene compounds are provided. The novel compounds are of the general formula:

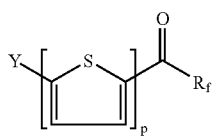

I wherein Y is a hydrogen atom, a halogen atom, an alkyl group, and aryl group or a perfluoroether acyl group, p is at least one, preferably at least two, and $R_f$ is a perfluoroether group.

Preferred α,ω-bis-perfluoroether acyl oligothiophene compounds are provided. The novel compounds are of the general formula:

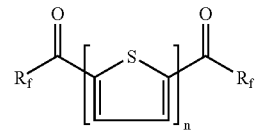

II wherein each $R_f$ is a perfluoroether group, and n is at least 2.

The present invention provides semiconductor devices and methods of preparing semiconductor devices that include a semiconductor layer that contains a perfluoroether acyl (oligo)thiophene compound. Suitable thiophene groups include those having two to six successively linked thiophene rings.

Definition

As used herein, the terms "a", "an", and "the" are used interchangeably with "at least one" to mean one or more of the elements being described.

"Alkyl" means a saturated monovalent hydrocarbon radical having from one to about twelve carbon atoms or a branched saturated monovalent hydrocarbon radical having from three to about twelve carbon atoms, e.g., methyl, ethyl, 1-propyl, 2-propyl, pentyl, and the like.

"Alkylene" means a saturated divalent hydrocarbon radical having from one to about twelve carbon atoms or a branched saturated divalent hydrocarbon radical having from three to about twelve carbon atoms, e.g., methylene, ethylene, propylene, 2-methylpropylene, pentylene, hexylene, and the like.

"Alkyleneoxy" has essentially the meaning given above for alkylene except the alkylene group is terminated by an oxygen atom, e.g., —$CH_2CH_2O$—, —$CH_2CH_2CH_2O$—, —$CH_2CH_2CH_2CH_2O$—, —$CH_2CH(CH_3)CH_2O$—, and the like.

The term "aryl" refers to monovalent unsaturated aromatic carbocyclic radicals having a single ring, such as phenyl, or multiple condensed rings, such as naphthyl or anthryl.

As used herein, the term "oligothiophene" refers to oligomers having at least two thiophene repeat units, linked by a covalent bond at the successive 2 positions. "(Oligo) thiophene" shall be inclusive of thiophene compounds having one thiophene ring and oligomeric thiophene compounds (oligothiophenes) having two or more thiophene rings.

"Perfluoroalkyl" has essentially the meaning given above for "alkyl" except that all or essentially all of the hydrogen atoms of the alkyl radical are replaced by fluorine atoms and the number of carbon atoms is from 1 to about 12, e.g. perfluoropropyl, perfluorobutyl, perfluorooctyl, and the like.

"Perfluoroalkylene" has essentially the meaning given above for "alkylene" except that all or essentially all of the hydrogen atoms of the alkylene radical are replaced by fluorine atoms, e.g., perfluoropropylene, perfluorobutylene, perfluorooctylene, and the like.

"Perfluoroalkyloxy" has essentially the meaning given above for "alkyloxy" except that all or essentially all of the hydrogen atoms of the alkyoxy radical are replaced by fluorine atoms and the number of carbon atoms is from 3 to about 12, e.g. $CF_3CF_2O$—, $CF_3CF_2CF_2CF_2O$—, $C_3F_7CF(CF_3)O$—, and the like.

"Perfluoroalkyleneoxy" has essentially the meaning given above for "alkyleneoxy" except that all or essentially all of the hydrogen atoms of the alkyleneoxy radical are replaced by fluorine atoms, e.g. —CF$_2$O—, —CF$_2$CF$_2$O—, —CF$_2$CF(CF$_3$)O—, and the like.

"Perfluoroether" is a saturated, perfluoroinated monovalent alkyl radical having from 2 to about 50 carbon atoms and at least one ether oxygen atom, e.g. CF$_3$CF$_2$OCF$_2$—, CF$_3$CF$_2$CF$_2$CF$_2$OCF$_2$CF$_2$—, CF$_3$CF(CF$_3$)O CF$_2$CF$_2$OCF$_2$CF$_2$—, CF$_3$CF(CF$_3$)O—[CF(CF$_3$)—CF$_2$O]$_n$—CF(CF$_3$)—, and the like. "Perfluoroether" is inclusive of perfluoro monoethers and perfluoro polyethers.

Semiconductor Devices

Semiconductor devices are provided that have a semiconductor layer that contains compound of the formula

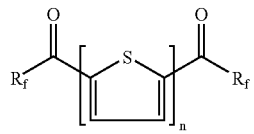

II wherein each R$_f$ is a perfluoroether group, and n is at least 2, preferably 3 to 6. R$_f$ may be a monoether or a polyether, i.e. a monovalent perfluoroalkoxyalkylene group or a monovalent perfluoropolyether group.

The perfluoroheteroalkyl group, R$_f$, of the fluorinated ether of Formulas I and II preferably corresponds to the formula:

R$_f^1$—O—(R$_f^2$)$_x$—(R$_f^3$)— (III)

wherein R$_f^1$ represents a perfluoroalkyl group having 1 to 10 carbon atoms, preferably 1 to 6 carbon atoms, (R$_f^2$)$_x$ represents a perfluoropolyalkyleneoxy group consisting of perfluoroalkyleneoxy groups, R$_f^2$, having 1 to 10 perfluorinated carbon atoms, preferably 1 to 6 carbon atoms, R$_f^3$ represents a perfluoroalkylene group having 1 to 10 perfluorinated carbon atoms, preferably 1 to 6 carbon atoms, and x is 0 to 25, preferably at least one, more preferably 1 to 4. The perfluoroalkyl and perfluoroalkylene groups in formula (III) may be linear or branched. A typical perfluoroalkyl group is CF$_3$—CF$_2$—CF$_2$—. For example, R$_f^3$ is —CF$_2$— or —CF(CF$_3$)—.

Examples of perfluoroalkyl groups R$_f^1$ include CF$_3$—CF$_2$—, CF$_3$—CF(CF$_3$)—, CF$_3$—CF$_2$—CF$_2$—, CF$_3$—, CF$_3$—CF$_2$CF$_2$—CF(CF$_3$)—, CF$_3$—CF$_2$CF(C$_3$F$_7$)—, CF$_3$—CF(C$_3$F$_7$)CF$_2$—, and CF$_3$—CF$_2$—CF$_2$—CF$_2$—.

Examples of perfluoroalkyleneoxy groups of perfluorinated polyalkyleneoxy group R$_f^2$ include: —CF$_2$—CF$_2$—O—, —CF(CF$_3$)—CF$_2$—O—, —CF$_2$—CF(CF$_3$)—O—, —CF$_2$—CF$_2$—CF$_2$—O—, —CF$_2$—O—, —CF(CF$_3$)—O—, and —CF$_2$—CF$_2$—CF$_2$—CF$_2$—O—.

Examples of perfluoroalkylene groups, R$_f^3$ include: —CF$_2$—CF$_2$—, —CF(CF$_3$)—CF$_2$—, —CF$_2$—CF(CF$_3$)—, —CF$_2$—CF$_2$—CF$_2$—, —CF$_2$—, —CF(CF$_3$)—, and —CF$_2$—CF$_2$—CF$_2$—CF$_2$—.

The perfluoroalkyleneoxy group, R$_f^2$, may be comprised of the same perfluoroalkyleneoxy units or of a mixture of different perfluoroalkyleneoxy units. When the perfluoroalkyleneoxy group is composed of different perfluoroalkylene oxy units, they can be present in a random configuration, alternating configuration or they can be present as blocks. Typical examples of perfluoropolyalkyleneoxy groups include —[CF$_2$—CF$_2$—O]$_n$—; —[CF(CF$_3$)—CF$_2$—O]$_n$—; —[CF$_2$CF$_2$—O]$_i$—[CF$_2$O]$_j$— and —[CF$_2$—CF$_2$—O]$_l$—[CF(CF$_3$)—CF$_2$—O]$_m$—; wherein n is an integer of 1 to 25, and i, l, m and j each are integers of 1 to 25.

In a particular embodiment, the fluorinated polyether, R$_f$, corresponds to the following formula (IV):

R$_f^1$—O—[CF(CF$_3$)—CF$_2$O]$_x$—CF(CF$_3$)— (IV)

wherein R$_f^1$ represents a perfluorinated alkyl group, e.g., a linear or branched perfluorinated alkyl group having 1 to 6 carbon atoms, x is an integer of 0 to 25, preferably at least one, more preferably 1 to 4. A preferred perfluorinated polyether group that corresponds to formula (IV) is CF$_3$—CF(CF$_3$)—O—[CF(CF$_3$)—CF$_2$O]$_x$—CF(CF$_3$)— wherein x is an integer of 1 to 4. This perfluoropolyether can be derived from an oligomerization of hexafluoropropylene oxide.

Preferred perfluoroether groups, R$_f$, are dimers, trimers and tetramers derived from the hexafluoropropylene oxide (HFPO) and correspond to the structures:

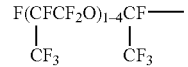

F(CFCF$_2$O)$_{1-4}$CF—
   |              |
   CF$_3$        CF$_3$

The corresponding acids, acid halides and esters may be prepared from the oligomerization of hexafluoropropylene oxide, or the oxidative oligomerization of hexafluoropropylene, such as is known in the art. Many of these compounds are commercially available from Matrix Scientific, Columbia, S.C.

Compounds according to formula (IV) can for example be obtained by oligomerization of hexafluoropropylene oxide, which results in a perfluoropolyether carbonyl fluoride. This carbonyl fluoride may be converted into an acid, or ester by reactions well known to those skilled in the art. The carbonyl fluoride or acyl fluoride, acid, or ester derived therefrom may then be reacted further to introduce the desired perfluoroether groups into the oligothiophene compounds according to known acylation procedures. For example, U.S. Pat. No. 6,127,498 or U.S. Pat. No. 3,536,710 describe suitable methods to produce compounds according to formula (IV) having desired acyl moieties.

Further details concerning the materials and procedures for the preparation of perfluorinated polyethers can be found in, for example, U.S. Pat. No. 3,242,218 (Miller); U.S. Pat. No. 3,322,826 (Moore); U.S. Pat. No. 3,250,808 (Moore et al.); U.S. Pat. No. 3,274,239 (Selman); U.S. Pat. No. 3,293,306 (Le Bleu et al.); U.S. Pat. No. 3,810,874 (Mitsch et al.); U.S. Pat. No. 3,544,537 (Brace); U.S. Pat. No. 3,553,179 (Bartlett); U.S. Pat. No. 3,864,318 (Caporiccio et al.); U.S. Pat. No. 4,321,404 (Williams et al.), U.S. Pat. No. 4,647,413 (Savu); U.S. Pat. No. 4,818,801 (Rice et al.); U.S. Pat. No. 4,472,480 (Olson); U.S. Pat. No. 4,567,073 (Larson et al.); U.S. Pat. No. 4,830,910 (Larson); U.S. Pat. No. 5,362,919 (Costello) U.S. Pat. No. 5,578,278 (Fall) and U.S. Pat. No. 5,306,758 (Pellerite), the disclosures of which are incorporated herein by reference. See also Patricia M. Savu, Fluorinated Higher Carboxylic Acids, 11 Kirk-Othmer Encyclopedia of Chemical Technology 551–58 (4th ed. 1994).

Perfluoroether acyl (oligo)thiophene compounds of Formula I, where Y is not a perfluoroether acyl group, may be prepared as follows. Thiophene (Y=H) may be treated with an alkyl lithium reagent, followed by acylation with a perfluoroether ester (in presence of a Lewis acid catalyst such as BF$_3$-Et$_2$O) to produce the mono perfluoroether acyl compound. The corresponding 5-alkyl or 5-aryl compounds (Y=alkyl or aryl) may be prepared by an analogous route starting from 2-alkyl or 2-aryl thiophene (such as are known in the art), followed by acylation and optional bromination. The corresponding 2-bromo-5-perfluoroether acyl compound may be prepared by monoacylation of 2,5-dibromothiophene to directly produce the 2-bromo-5-perfluoroether acyl compound.

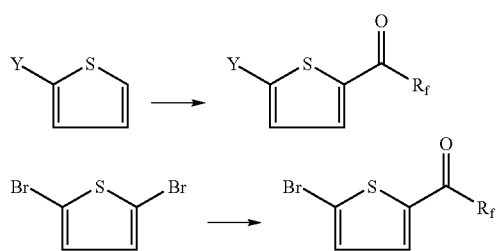

Higher thiophene compounds, where Y is H, halogen, alkyl or aryl may be prepared by Stille coupling of a thienyl stannane with an α-bromo-ω-perfluoroether acyl thiophene according to the following general scheme:

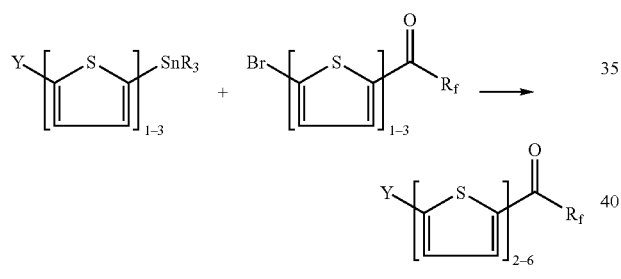

Preferred α,ω-bis-perfluoroether acyl oligothiophene compounds of Formula II may be prepared according to Reaction Scheme A by a Stille coupling reaction. Generally, the oligothiophenes may be prepared by reacting a bis(trialkylstannyl)thiophene (such as a 2,5-bis(trialkylstannyl) thiophene or a 5,5'-bis(trialkylstannyl)bithiophene) with a 2-perfluoroether acyl 5-halothiophene (or a 5-perfluoroether acyl 5'-halobithiophene) in the presence of a palladium catalyst.

A 2-halo-5-perfluoroetheracyl thiophene (such compounds of formulas VI) or a 5-halo-5'-perfluoroetheracyl-bithiophene (such compounds of formulas X) can be reacted with a bis(trialkylstannyl) compound (i.e., Formula V or VIII, where R is an alkyl group) to form a α,ω-bis(2-perfluoroetheracyl oligothiophene (i.e., Formula VII, IX, XI or XII). The Stille coupling reaction may be performed as outlined in Farina V. and Krishnamurthy, V. in Organic Reactions; L. A. Paquette, Ed., John Wiley and Sons., 1997; vol. 50, pp. 1–652. The reaction products may be purified to a semiconductor grade material by any known process such as by vacuum sublimation.

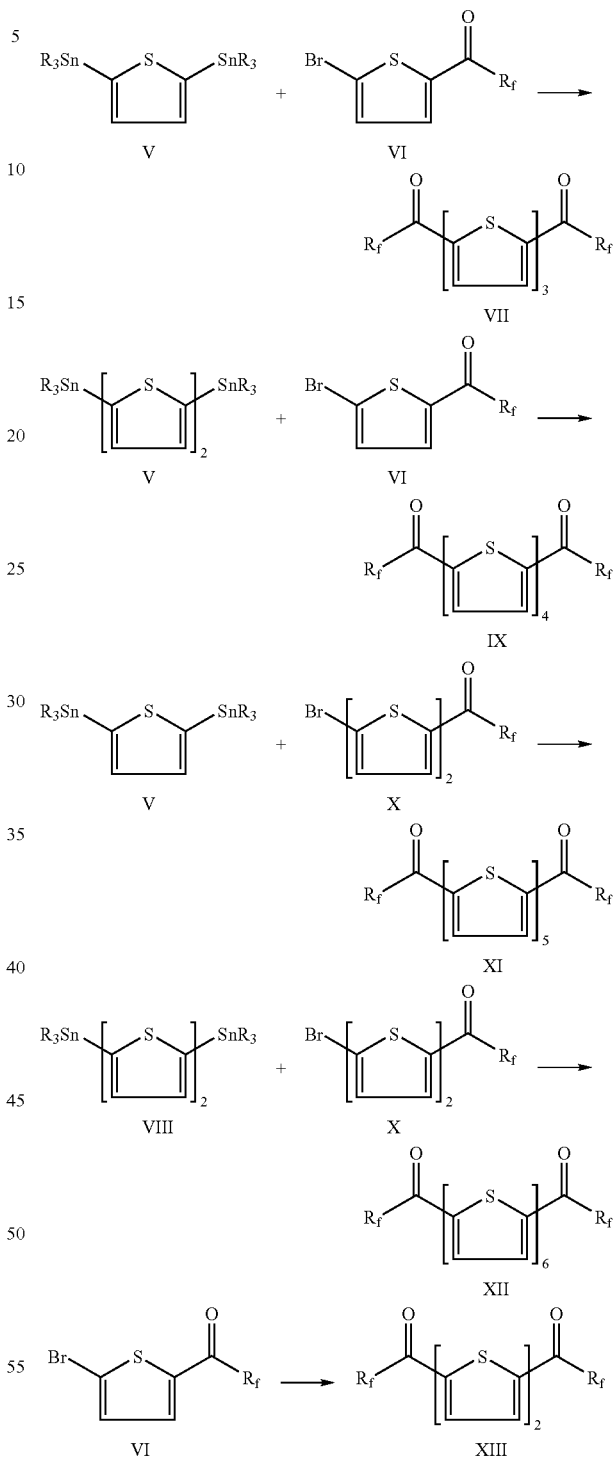

The bis-trialkylstannyl thiophene compounds of formulas V and VIII are known. Reference may be made to Y. Wei et al. Chem. Mater. Vol. 8, 1996, pp. 2659–2666.

The monoacyl compound of formula VI may be made by treatment of 2,5-dihalothiophene with an alkyl lithium compound, to produce the 2-bromo-5-lithio thiophene, followed by reaction with a perfluorinated ether ester (or equivalent)

in the presence of boron trifluoride etherate. This method yields the desired product V in high yields, and has proven superior to other known methods, such as formation of the cuprate, followed by reaction with a perfluorinated acyl compound.

The monoacyl bithiophene compound X may be prepared by a two-step synthesis comprising first reacting 5-lithio-2,2'-bithiophene (generated in situ) with a perfluorinated ether ester (or equivalent) in the presence of boron trifluoride etherate), followed by bromination, such as by N-bromosuccinimide.

With reference to compounds VI and X, 5-halo-5'-perfluoroether acyl thiophene compounds are useful in the preparation of the bis-perfluoroether thiophene compounds of the present invention. Such novel compounds are of the general formula:

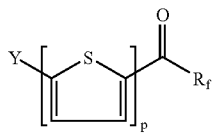

where Y is H, a halogen, an aryl or an alkyl group, $R_f$ is a perfluoroether group and p is 1 to 6 Compounds where p is 2 or greater may be prepared by a Stille coupling reaction of a compound of formula VI or X with a mono-trialkylstannyl thiophene or a mono-trialkylstannyl bithiophene, followed by halogenation of the ω-5 position of the terminal thiophene ring.

The bithiophene compound of formula XIII may be prepared by coupling of the 5-bromo-2-thienyl magnesium bromide and a perfluoroether acid halide according to the procedure described in Portnoy, J. Org. Chem, vol. 32, 1967, pp 233–4. The Ullman coupling reactions may also prove useful.

Asymmetric α,ω-bis-perfluoroether acyl oligothiophenes (i.e., a oligothiophenes with different perfluoroether acyl groups can be prepared, for example, through using a mixture of compounds of Formulas VI or X having different $R_f$ groups, although a mixture of products will result. With respect to each of the reaction schemes, the preferred bromo-substituted thiophenes are illustrated, but other halides may also be used.

Other synthetic approaches can be used to prepare α,ω-bis-perfluoroether acyl oligothiophene compounds. For example, the thiophene-2-aldehyde may be reacted with a perfluoroether organometallic compounds (such as $R_f$—Li, generated in situ) to produce the alcohol shown. This may be brominated at the 5-position, followed by oxidation of the hydroxyl group to the ketone. Reference may be made to the general methods described in U.S. Pat. Nos. 6,608,323 and 6,585,914 (Marks et al.).

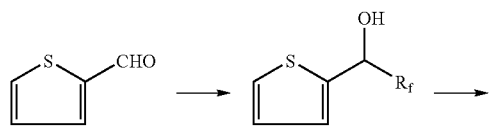

VI

-continued

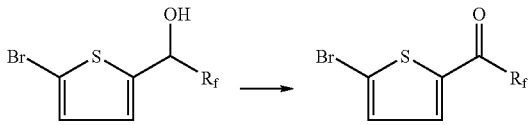

The compounds of the invention may be used as a n-channel semiconductor. The semiconductor layer that contains a α,ω-bis-perfluoroether acyl oligothiophene compound can be included in any type of semiconductor device. Semiconductor devices have been described, for example, by S. M. Sze in *Physics of Semiconductor Devices*, $2^{nd}$ edition, John Wiley and Sons, New York (1981). Such devices may include rectifiers, transistors (of which there are many types, including p-n-p, n-p-n, and thin-film transistors), photoconductors, current limiters, thermistors, p-n junctions, field-effect diodes, Schottky diodes, and the like.

Semiconductor devices can include components such as transistors, arrays of transistors, diodes, capacitors, embedded capacitors, and resistors that are used to form circuits. Semiconductor devices also can include arrays of circuits that perform an electronic function. Examples of these arrays, or integrated circuits, are inverters, oscillators, shift registers, and logic. Applications of these semiconductor devices and arrays include radio frequency identification devices (RFIDs), smart cards, displays backplanes, sensors, memory devices, and the like.

Each semiconductor device contains a semiconductor layer with a compound according to Formulas I or II. The semiconductor layer can be combined with a conductive layer, a dielectric layer, or a combination thereof to form the semiconductor device. Semiconductor devices can be prepared or manufactured by known methods such as, for example, those described by Peter Van Zant in *Microchip Fabrication*, Fourth Edition, McGraw-Hill, New York (2000).

Some of the semiconductor devices are organic thin-film transistors. One embodiment of an organic thin-film transistor 10 is shown in FIG. 1a. The organic thin-film transistor (OTFT) 10 includes an optional substrate 12, a gate electrode 14 disposed on the optional substrate 12, a gate dielectric material 16 disposed on the gate electrode 14, an optional surface treatment layer 18 disposed on the gate dielectric layer 16, a source electrode 22, a drain electrode 24, and a semiconductor layer 20 that is in contact with both the source electrode 22 and the drain electrode 24. The source electrode 22 and the drain electrode 24 are separated from each other in an area on the surface of the semiconductor layer 20 (i.e., the source electrode 22 does not contact the drain electrode 24). The portion of the semiconductor layer that is positioned between the source electrode and the drain electrode is referred to as the channel 21. The channel is positioned over the gate electrode 14, the gate dielectric layer 16, and the optional surface treatment layer 18. The semiconductor layer 20 contacts the gate dielectric layer 16 or the surface treatment layer 18.

Figure 1B:
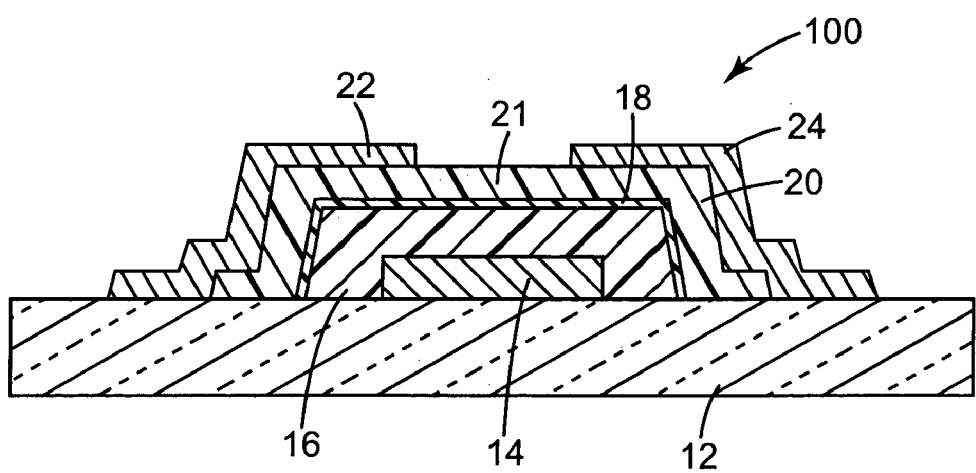

A second embodiment of an organic thin-film transistor is shown in FIG. 1b. This OTFT 100 includes a gate electrode 14 disposed on an optional substrate 12, a gate dielectric layer 16 disposed on the gate electrode 14, an optional surface treatment layer 18 disposed on the gate dielectric layer 16, a semiconductor layer 20, and a source electrode 22 and a drain electrode 24 disposed on the semiconductor layer 20. In this embodiment, the semiconductor layer 20 is between the gate dielectric layer 16 and both the source electrode 22 and the drain electrode 24. The semiconductor layer 20 can contact the gate dielectric layer 16 or the optional surface treatment layer 18. The source electrode 22 and the drain electrode 24 are separated from each other (i.e., the source electrode 22 does not contact the drain electrode 24) in an area on the surface of the semiconductor layer 20. The channel 21 is the portion of the semiconductor layer that is positioned between the source electrode 22 and the drain electrode 24. The channel 21 is positioned over the gate electrode 14, the gate dielectric layer 16, and the optional surface treatment layer 18.

In operation of the semiconductor device configurations shown in FIGS. 1a and 1b, voltage can be applied to the drain electrode 24. However, no charge (i.e., current) is passed to the source electrode 22 unless positive voltage is also applied to the gate electrode 14, relative to the source electrode 22. That is, unless voltage is applied to the gate electrode 14, the channel 21 in the semiconductor layer 20 remains in a non-conductive state. Upon application of voltage to the gate electrode 14, the channel 21 becomes conductive and charge flows through the channel 21 from the source electrode 22 to the drain electrode 24.

A substrate 12 often supports the OTFT during manufacturing, testing, and/or use. Optionally, the substrate can provide an electrical function for the OTFT. For example, the backside of the substrate can provide electrical contact. Useful substrate materials include, but are not limited to, inorganic glasses, ceramic materials, polymeric materials, filled polymeric materials (e.g., fiber-reinforced polymeric materials), metals, paper, woven or non-woven cloth, coated or uncoated metallic foils, or a combination thereof. Suitable polymeric substrates include acrylics, epoxies, polyamides, polycarbonates, polyimides, polyketones, polynorbornenes, polyphenyleneoxides, poly(ethylene naphthalate), poly(ethylene terephthal ate), poly(phenylene sulfide), poly(ether ether ketones) such as poly(oxy-1,4-phenyleneoxy-1,4-phenylenecarbonyl-1,4-phenylene), and the like.

The gate electrode 14 can include one or more layers of a conductive material. For example, the gate electrode can include a doped silicon material, a metal, an alloy, a conductive polymer, or a combination thereof. Suitable metals and alloys include, but are not limited to, aluminum, chromium, gold, silver, nickel, palladium, platinum, tantalum, titanium, indium tin oxide (ITO) or a combination thereof. Exemplary conductive polymers include, but are not limited to, polyaniline or poly(3,4-ethylenedioxythiophene)/poly(styrene sulfonate). In some organic thin film transistors, the same material can provide both the gate electrode function and the support function of the substrate. For example, doped silicon can function as both the gate electrode and as a substrate.

The gate dielectric layer 16 is disposed on the gate electrode 14. This gate dielectric layer 16 electrically insulates the gate electrode 14 from the balance of the OTFT device. Useful materials for the gate dielectric include, for example, an inorganic dielectric material, a polymeric dielectric material, or a combination thereof. The gate dielectric can be a single layer or multiple layers of suitable materials. Each layer in a single or multilayer dielectric can include one or more dielectric materials.

Exemplary inorganic dielectric materials include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, zinc sulfide, hafnium oxides, and the like. In addition, alloys, combinations, and multiple layers of these materials can be used for the gate dielectric layer 16.

Exemplary polymeric dielectric materials include polyimides, parylene C, crosslinked benzocyclobutene, cyanoethylpullulan, polyvinyl alcohol, and the like. See, for example, C. D. Sheraw et al., "Spin-on polymer gate dielectric for high performance organic thin film transistors", *Materials Research Society Symposium Proceedings*, vol. 558, pages 403–408 (2000), Materials Research Society, Warrendale, Pa., USA; and U.S. Pat. No. 5,347,144 (Gamier).

Other exemplary organic polymeric dielectrics include cyano-functional polymers such as cyano-functional styrenic copolymers as disclosed in U.S. patent application Ser. No. 10/434,377, filed May 8, 2003, the disclosure of which is incorporated herein by reference. Some of these polymeric materials can be coated from solution, can be crosslinked, can be photo-patterned, can have high thermal stability (e.g., stable up to a temperature of about 250° C.), can have a low processing temperature (e.g., less than about 150° C. or less than about 100° C.), can be compatible with flexible substrates, or combinations thereof.

Exemplary cyano-functional polymers that can be used as organic dielectric materials include, but are not limited to, styrene maleic anhydride copolymers modified by adding a methacrylate functional group for crosslinking purposes and by attaching cyano-functional groups; the reaction product of bis(2-cyanoethyl)acrylamide with an acrylated polystyrene macromer; polymers formed from 4-vinylbenzylcyanide; polymers formed from 4-(2,2'-dicyanopropyl)styrene; polymers formed from 4-(1,1',2-tricyanoethyl)styrene; and polymers formed from 4-(bis-(cyanoethyl)aminoethyl)styrene; and a copolymer formed from 4-vinylbenzylcyanide and 4-vinylbenzylacrylate.

The organic thin film transistors can include an optional surface treatment layer 18 disposed between the gate dielectric layer 16 and at least a portion of the organic semiconductor layer 20. In some embodiments, the optional surface treatment layer 18 serves as an interface between the gate dielectric layer and the semiconductor layer. The surface treatment layer can be a self-assembled monolayer or a polymeric material.

Suitable self-assembled monolayer surface treatment layers are disclosed, for example, in U.S. Pat. No. 6,433,359 B1 (Kelley et al.). Exemplary self-assembled monolayers can be formed from 1-phosphono-2-ethylhexane, 1-phosphono-2,4,4-trimethylpentane, 1-phosphono-3,5,5-trimethylhexane, 1-phosphonoctane, 1-phosphonohexane, 1-phosphonohexadecane, 1-phosphono-3,7,11,5-tetramethylhexadecane, and the like.

Useful polymers and copolymers for a surface treatment layer are usually non-polar, glassy solids at room temperature. The polymeric materials in this layer typically have glass transition temperature ($T_g$) measured in the bulk of at least 25° C., of at least 50° C., or of at least 100° C. Suitable polymeric surface treatment layers are described, for example, in U.S. Patent Application Publication 2003/0102471 A1 (Kelley et al.) and U.S. Pat. No. 6,617,609 (Kelley et al.)

Exemplary polymeric surface treatment layers can contain polystyrene, polyfluorene, polynorbomene, poly(1-hexene), poly(methyl methacrylate), poly(acenaphthylene), poly(vinylnaphthalene), poly(butadiene), and poly(vinyl acetate). Other exemplary polymeric surface treatment layers can contain polymers or copolymers derived from α-methylstyrene, 4-tert-butylstyrene, 2-methylstyrene, 3-methylstyrene, 4-methylstyrene, 4-(phosphonomethyl)styrene, divinyl benzene, and combinations thereof. Examples of still other useful polymeric materials for the surface treatment layer include poly(dimethylsiloxane), poly(dimethylsiloxane-co-diphenylsiloxane), poly(methylphenylsiloxane-co-diphenylsiloxane), poly(dimethylsiloxane-co-methylphenylsiloxane), and the like.

The surface treatment layer often has a maximum thickness less than 400 Angstroms (Å). For example, the surface treatment layer can be less than 200 Å, less than 100 Å, or less than 50 Å. The surface treatment layer generally has a thickness of at least about 5 Å, at least about 10 Å, or at least 20 Å. The thickness can be determined through known methods such as ellipsometry.

The source electrode 22 and drain electrode 24 can be metals, alloys, metallic compounds, conductive metal oxides, conductive ceramics, conductive dispersions, and conductive polymers, including, for example, gold, silver, nickel, chromium, barium, platinum, palladium, aluminum, calcium, titanium, indium tin oxide (ITO), fluorine tin oxide (FTO), antimony tin oxide (ATO), indium zinc oxide (IZO), poly(3,4-ethylenedioxythiophene)/poly(styrene sulfonate), polyaniline, other conducting polymers, alloys thereof, combinations thereof, and multiple layers thereof. Some of these materials are appropriate for use with n-type semiconductor materials and others are appropriate for use with p-type semiconductor materials, as is known in the art.

The thin film electrodes (e.g., the gate electrode, the source electrode, and the drain electrode) can be provided by any means known in the art such as physical vapor deposition (for example, thermal evaporation or sputtering), ink jet printing, or the like. The patterning of these electrodes can be accomplished by known methods such as shadow masking, additive photolithography, subtractive photolithography, printing, microcontact printing, and pattern coating.

The semiconductor devices that contain the perfluoroether acyl oligothiophene compounds tend to have performance characteristics such as charge-carrier mobility and current on/of ratio that are comparable to known organic semiconductor devices such as those that contain pentacene. For example, semiconductor devices can be prepared that have an n-channel mobility of about 1 cm$^2$/volt-sec and on-off ratio greater than about $10^5$.

In another aspect, a method of preparing a semiconductor device is provided. The method involves preparing a semiconductor layer that contains a perfluoroether acyl oligothiophene compound of Formulas I or II, where n is preferably 3 to 6. The semiconductor layer is usually formed using a vapor deposition process.

In some exemplary methods of preparing a semiconductor device, the method involves preparing a semiconductor layer that contains a perfluoroether acyl oligothiophene compound of Formulas I or II; and depositing a dielectric layer, a conductive layer, or a combination thereof adjacent to the semiconductor layer. As used herein, the term "adjacent" refers to a first layer that is positioned near a second layer. The first layer often contacts the second layer but another layer could be positioned between the first and second layer. No specific order of preparing or depositing is necessary; however, the semiconductor layer is often prepared on the surface of another layer such as the dielectric layer, conductive layer, or a combination thereof.

One exemplary method of preparing a semiconductor device provides an organic thin film transistor. The method includes preparing a semiconductor layer that contains a perfluoroether acyl oligothiophene compound of Formulas I or II; positioning a source electrode and a drain electrode on a surface of the semiconductor layer such that the source electrode and the drain electrode are separated in an area on the surface of the semiconductor layer (i.e., the source electrode does not contact the drain electrode). The method can further include providing a gate dielectric layer, a gate electrode, and an optional surface treatment layer.

More specifically, an organic thin film transistor can be prepared by providing a gate electrode; depositing a gate dielectric layer on a surface of the gate electrode; preparing a semiconductor layer adjacent to the gate dielectric layer (i.e., the gate dielectric is positioned between the gate electrode and the semiconducting layer); and positioning a source electrode and a drain electrode on a surface of the semiconductor layer that is opposite the gate dielectric layer. The source electrode and the drain electrode are separated from each other in an area on the surface of the semiconductor layer.

In one embodiment of this method, the various layers of the semiconductor device are arranged in the following order: gate electrode; gate dielectric layer; semiconductor layer; and a layer containing a source electrode and a drain electrode. In another embodiment, the various layers of the semiconductor device are arranged in the following order: gate electrode, gate dielectric layer, surface treatment layer, semiconductor layer, and a layer containing a source electrode and a drain electrode. The source electrode does not contact the drain electrode in these embodiments. That is, the source electrode and the drain electrode are separated from each other in an area on the surface of the semiconductor device. One surface of the semiconductor layer contacts both the source electrode and the drain electrode while the opposite surface of the semiconductor layer contacts the gate dielectric layer or the surface treatment layer.

The organic thin film transistor exemplified in FIG. 1b can be prepared by providing a substrate, depositing a gate electrode on the substrate, depositing a gate dielectric layer on a surface of the gate electrode such that the gate electrode is positioned between the substrate and the gate dielectric layer; applying a surface treatment layer to a surface of the gate dielectric layer opposite the gate electrode; preparing a semiconductor layer on a surface of the surface treatment layer opposite the gate dielectric layer; and positioning a source electrode and a drain electrode on a surface of the semiconductor layer that is opposite the polymeric treatment layer. The source electrode and the drain electrode are separated from each other in an area on the surface of the semiconductor layer. The area of separation between the source electrode and the drain electrode can define a channel in the semiconductor layer.

Another organic thin film transistor can be prepared by providing a gate electrode; depositing a gate dielectric layer on a surface of the gate electrode; positioning a source electrode and a drain electrode adjacent to the gate dielectric material such that the source electrode and the drain electrode are separated from each other in an area over the gate dielectric layer; preparing a semiconductor layer that is deposited on the source electrode, drain electrode, and in the area between the source electrode and the drain electrode. The semiconductor layer contacts both the source electrode and the drain electrode. The portion of the semiconductor layer that is positioned in the area between the source electrode and the drain electrode defines the channel.

In one embodiment of this method, the various layers of the semiconductor device are arranged in the following order: gate electrode; gate dielectric layer; a layer containing a source electrode and a drain electrode; and a semiconductor layer. In another embodiment, the various layers of the semiconductor device are arranged in the following order: gate electrode; gate dielectric layer; surface treatment layer;

a layer containing a source electrode and a drain electrode; and semiconductor layer. The source electrode does not contact the drain electrode in these embodiments. A portion of the semiconductor layer can extend between the source electrode and the drain electrode.

The organic thin film transistor exemplified in FIG. 1a can be prepared by providing a substrate, depositing a gate electrode on the substrate, depositing a gate dielectric layer on a surface of the gate electrode such that the gate electrode is positioned between the substrate and the gate dielectric layer; applying a surface treatment layer to a surface of the gate dielectric layer opposite the gate electrode; positioning a source electrode and a drain electrode on a surface of the polymeric treatment layer such that the two electrodes are separated from each other in an area; preparing a semiconductor layer on the source electrode, drain electrode, and in the area between the source electrode and the drain electrode. The semiconductor layer contacts both the source electrode and the drain electrode. The portion of the semiconductor layer that is positioned in the area between the source electrode and the drain electrode defines a channel in the semiconductor layer.

The organic thin film transistors or other semiconductor devices such as integrated circuits can be prepared using flexible, repositionable polymeric aperture masks. The technique involve sequentially depositing material through a number of polymeric aperture masks formed with patterns that define layers, or portions of layers, of the semiconductor device. The use of such polymeric aperture masks are further described in U.S. Patent Publication Nos. 2003/0094959-A1, 2003/0150384-A1, 2003/0152691-A1, and 2003/0151118-A1, incorporated herein by reference.

Repositionable polymeric aperture masks often have a thickness of 5 to 50 micrometers or 15 to 35 micrometers. The various deposition apertures in the aperture masks usually have widths less than 1000 micrometers, less than 50 micrometers, less than 20 micrometers, less than 10 micrometers, or even less than 5 micrometers. Apertures of these sizes are particularly useful in creating small circuit elements for integrated circuits. Moreover, one or more gaps between deposition apertures are typically less than 1000 micrometers, less than 50 micrometers, less than 20 micrometers, or less than 10 micrometers, which is also useful in creating small circuit elements. The aperture masks can have a pattern with a width greater than 1 centimeter, 25 centimeters, 100 centimeters, or even 500 centimeters. Patterns having these widths can be useful in creating various circuits over a larger surface area.

Various laser ablation techniques may be used to facilitate the creation of polymeric aperture masks having patterns of deposition apertures. In addition, stretching techniques and other techniques may be used to facilitate alignment of flexible polymeric aperture masks. Furthermore, methods of controlling sag in aperture masks may be used which can be particularly useful in using masks that include a pattern that extends over a large width.

Other methods known in the art can be used to prepare the semiconductor devices. These methods include, for example, metal shadow masks; photolithography and/or etching; and printing methods such as inkjet, screen-printing, gravure printing, and the like.

In some methods that involve the use of aperture masks, semiconductor devices (e.g., integrated circuits) can be created solely using aperture mask deposition techniques, without requiring any of the etching or photolithography steps typically used to form such devices. The techniques can be particularly useful in creating circuit elements for electronic displays such as liquid crystal displays and low-cost integrated circuits such as radio frequency identification (RFID) circuits. In addition, such techniques can be advantageous in the fabrication of integrated circuits incorporating organic semiconductors, which typically are not compatible with photolithography or other wet chemical processes.

EXAMPLES

Objects and advantages of this invention are further illustrated by the following examples, but the particular materials and amounts thereof recited in these examples, as well as other conditions and details, should not be construed to unduly limit this invention.

All reactions were carried out under nitrogen. Melting points were determined by DSC analyses under $N_2$ at a ramp rate of 20° C./min and are reported as the range between the onset temperature and the peak maximum. Combustion analyses were run using a LECO 932 CHNS elemental analyzer (LECO Corporation, St. Joseph, Mich. ). Infrared spectra were recorded using pellets pressed with KBr. Positive ion mass spectrometry was done using an Applied Biosystems Inc. DE/STR MALDI/TOF mass spectrometer (Applied Biosystems, Inc., Foster City, Calif.). Dilute $CHCl_3$ solutions of the samples were deposited directly on the probe tip without a matrix. $^1H$ and $^{19}F$ NMR spectra were collected in $d_6$-acetone at 200 MHz and 188 MHz, respectively, unless otherwise indicated. Internal tetramethylsilane and fluorotrichloromethane were referenced to 0.0 ppm. Silica gel for column chromatography was purchased from Aldrich (Milwaukee, Wis.; Merck, grade 9385, 230–400 mesh, 60 Å). Tetrahydrofuran (THF) and diethyl ether ($Et_2O$) were distilled from sodium/benzophenone ketyl. N,N-dimethylformamide (DMF) was vacuum distilled under nitrogen from $MgSO_4$ or purchases as anhydrous grade from Aldrich. All other solvents were used as obtained. Bithiophene, 2,5-dibromothiophene, 3-bromothiophene, boron trifluoride diethyl etherate, aluminum trichloride, n-butyl lithium (1.6 M or 2.5 M in hexanes), N-bromosuccimide (NBS), and dimethylamine borane were purchased from Aldrich. NBS was recrystallized from hot water and dried under vacuum prior to use. Perfluoro(2,5-dimethyl-3,6-dioxanonanoic) acid methyl ester (HFPO trimer carbomethoxylate), methyl 3,6-dioxadecanoate, and methyl 3,6,9-trioxadecanoate were purchased from Matrix Scientific (Columbia, S.C.) and used as received. Tetrakis (triphenylphosphine)palladium (0) was purchased from Strem Chemicals, Newburyport, Mass. 5,5'-bis(tri-n-butylstannyl)-2,2'-bithiophene and 5,5'-bis(tri-n-butylstannyl) thiophene were synthesized using the procedure published by Y. Wei, Y. Y and, and J. -M Yeh, Chem. Mater., 8, 2659–2666 (1996).

Example 1

5-Perfluoro(3,6,9-trioxadecanoyl)-2,2'-bithiophene

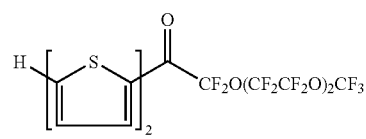

A hexanes solution of BuLi (10.18 mL, 16.3 mmol) was added drop wise to a cold (−70° C.) THF solution (250 mL) of bithiophene (2.71 g, 16.3 mmol). After 30 min, $CF_3$($OC_2F_4$)$_2OCF_2CO_2Me$ (7.66 g, 16.4 mmol) and $BF_3 \cdot OEt_2$ (2.5 mL, 19.6 mmol, 1.2 eq) were added sequentially and the mixture stirred at −70° C. for 90 min. A few mL of saturated $NH_4Cl$ (aq) were charged, the mixture was warmed to room temperature, and the volatile materials removed under reduced pressure. Et$_2$O (400 mL) and brine (250 mL) were charged and the reaction was stirred vigorously.

The mixture was filtered through a Celite pad and the amber organic washed with 2×100 mL brine, dried with MgSO$_4$, and filtered. The solvent was stripped and the material adsorbed onto silica gel. The crude product was purified by column chromatography (hexanes/EtOAc, 0%–3%) to afford 6.38 g (70%) of yellow product. Mp (ΔH): 50–53° C. (51 J/g). IR: 1684 (vco), 1505 w, 1450 m, 1423 w, 1229 s, 1193 s, 1139 s, 1103 s, 1077 s, 906 m, 869 m, 842 w, 803 m, 741 m, 706 s, 682 m, 619 w, 546 w, 522 w, 508 w, 453 w cm$^{-1}$. $^1$H NMR: δ 7.22 (dd, J=5.1 Hz, 3.8 Hz, 5'-H), 7.56 (d, J=4.3 Hz, 3-H), 7.67 (dd, J=3.7 Hz, 1.1 Hz, 4'-H), 7.73 (dd, J=5.1 Hz, 1.1 Hz, 3'-H), 8.01 (dt, J=4.3 Hz, 1.7 Hz, 4-H). $^{19}$F NMR: δ −55.03 (t, J=9.0 Hz, CF$_3$), −74.43 (m, 8-lines, COCF$_2$), −87.50 (m, 5 lines, CF$_2$), −88.16 (br, 2 CF$_2$ groups), −90.19 (q, J=9.4 Hz, CF$_2$OCF$_3$). Anal. Calcd for C$_{15}$H$_5$F$_{13}$O$_4$S$_2$: C, 32.15; H, 0.90; S, 11.45. Found: C, 32.2; H, 0.9; S, 11.6.

Example 2

5-Perfluoro(3,6-dioxadecanoyl)-2,2'-bithiophene

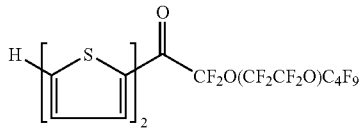

This compound was prepared analogously to Example 1. A reaction between BuLi (36.75 mL, 58.8 mmol) and bithiophene (9.75 g, 58.6 mmol) in cold THF (250 mL, −70° C.) was stirred for 30 min, followed by a sequential addition of C$_4$F$_9$OC$_2$F$_4$OCF$_2$CO$_2$Me (30.2 g, 65.7 mmol) and BF$_3$OEt$_2$ (9.0 mL, 71 mmol).

The material was purified by chromatography to afford 18.7 g (54%) of yellow product. Mp (ΔH): 50–53° C. (45 J/g). IR: 1666 m (v$_{CO}$), 1504 w, 1448 m, 1309 m, 1233 s, 1202 s, 1153 s, 1081 m, 1027 m, 993 m, 851 w, 837 w, 802 m, 763 w, 752 m, 802 m, 763 w, 752 m, 721 m, 710 m, 654 w, 616 w, 532 w, 460 w cm$^{-4}$. $^1$H NMR: δ 7.20 (dd, J=5.17 Hz, 3.8 Hz, 5'-H), 7.53 (d, J=4 Hz, 3-H), 7.64 (dd, J=4 Hz, 1 Hz, 4'-H), 7.69 (dd, J=5.1 Hz, 1.1 Hz, 3'-H), 7.98 (dt, J=4.2 Hz, 1.6 Hz, 4-H). $^{19}$F NMR: δ −74.46 (t, J=12.2 Hz, CF$_3$), −80.88 (br, COCF$_2$O), −83.08 (br, OCF$_2$CF$_2$O), −87.60 ('t', J=12.0 Hz, —OCF$_2$CF$_2$O), −88.05 ('t', J=12.7 Hz, OCF$_2$C$_3$F$_7$), −126.14 (m, CF$_2$CF$_2$CF$_2$CF$_3$). Anal. Calcd for C$_{16}$H$_5$F$_{15}$O$_3$S$_2$: C, 32.33; H, 0.85; S, 10.79. Found: C, 32.1; H, 0.8; S, 10.9.

Example 3

5-Perfluoro(2,5-dimethyl-3,6-dioxanonanoyl)-2,2'-bithiophene

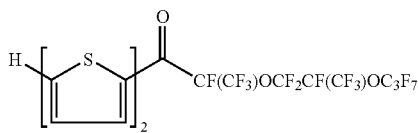

This compound was prepared analogously to Example 1. Reaction between bithiophene (7.90 g, 47.5 mmol), BuLi (47.6 mmol), HFPO trimer carbomethoxylate (26.7 g, 52.2 mmol), and BF$_3$OEt$_2$ (7.0 mL, 55 mmol) in 250 mL of cold THF yielded 24.8 g (81%) of product. Mp (ΔH):37–40° C. 37 (J/g). IR: 1666 s (v$_{CO}$), 1504 w, 1449 s, 1310 s, 1233 s, 1202 vs, 1153 s, 1081 m, 1027 m, 993 s, 897 w, 850 m, 837 m, 802 s, 763 m, 752 m, 721 m, 710 s, 654 m, 616 m, 532 m, 456 w cm$^{-1}$. $^1$H NMR: δ 7.23 (dd, J=4.0 Hz, 5.0 Hz, 5'-H), 7.59 (d, J=4.4 Hz, 3-H), 7.70 (dd, J=3.8 Hz, 1.2 Hz, 4'-H), 7.74 (dd, J=5.2 Hz, 1.2 Hz, 3'-H), 8.16 ('t', J=4.0 Hz, 4-H). $^{19}$F NMR: δ −76.8 to −82.1 (m, 4 F OCF$_2$CF(CF$_3$)OCF$_2$-), −79.8 (s, 3 F, CF$_2$CFCF$_3$), −81.1 (s, 6 F, COCFCF$_3$ and CF$_2$CF$_3$), −129.2 (br m, 1 F, COCFCF$_3$), −129.2 (s, 2 F, OCF$_2$CF$_2$CF$_3$), −144.6 (br m, 1 F, OCF$_2$CFCF$_3$O). A number of the resonances in the $^{19}$F NMR data are observed as pairs due to the asymmetric centers of the fluorinated group. Anal. calcd for C$_{17}$H$_5$F$_{17}$O$_3$S$_2$: C, 31.69; H, 0.78; S, 9.95. Found: C, 31.3; H, 0.8; S, 9.9.

Example 4

5-Bromo-5'-perfluoro(3,6,9-trioxadecanoyl)-2,2'-bithiophene.

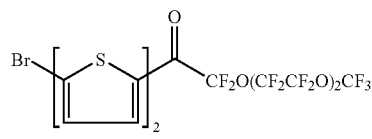

NBS (2.50 g, 13.32 mmol) was added to a stirred mixture of DMF (250 mL) and 5-perfluoro(3,6,9-trioxadecanoyl)-2,2'-bithiophene (6.22 g, 11.1 mmol) that was covered with aluminum foil. The solution was stirred overnight, poured into 500 mL of brine, and extracted with Et$_2$O (500 mL) and hexanes (250 mL). The yellow extract was separated, washed with 100 mL brine, 100 mL water, dried with MgSO$_4$, and filtered.

Concentration of the filtrate followed by cooling at −15° C. overnight afforded 5.32 g (75%) of bright yellow product. Mp (ΔH): 78–81° C. (47 J/g). IR: 1677 s (v$_{CO}$), 1509 w, 1452 m, 1421 m, 1231 s, 1191 s, 1153 s, 1104 s, 1076 s, 906 m, 891 m, 861 m, 837 w, 791 m, 740 m, 714 m, 683 m, 648 w, 545 w, 523 w, 510 w, 457 w cm$^{-1}$. $^1$H NMR: δ 7.30(d, J=4.0 Hz, 3'-H), 7.51 (d, J=4.0 Hz, 4-H), 7.56 (d, J=4.3 Hz, 3-H), 8.02 (dt, J=4.3 Hz, 1.4 Hz, 4'-H). $^{19}$F NMR: δ −55.03 (t, J=9.2 Hz, CF$_3$), −74.49 (m, COCF$_2$), −87.49 (m, CF$_2$), −88.15 (br 2 CF$_2$ groups), −90.19 (q, J=8.1 Hz, CF$_2$OCF$_3$). Anal. Calcd for C$_{15}$H$_4$BrF$_{13}$O$_4$S$_2$: C, 28.19; H, 0.63; S, 10.03. Found:C, 28.2; H, 0.4; S, 10.1.

Example 5

5-Bromo-5'-perfluoro(3,6-dioxadecanoyl)-2,2'-bithiophene

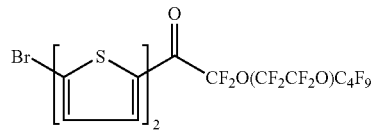

A DMF solution (200 mL) of 5-perfluoro(3,6-dioxadecanoyl)-2,2'-bithiophene (17.20 g, 28.94 mmol) was charged with NBS (6.70 g, 37.6 mmol) and stirred overnight covered with foil. Orange crystals of the product precipitated from the solution. Et$_2$O (200 mL) and brine (200 mL) were added to the reaction and the solution washed in a separatory funnel. The organic layer was separated and washed with 3×200 mL of brine.

The organic was dried with MgSO$_4$, filtered, and the volatile materials removed under reduced pressure to afford 18.63 g (96%) of yellow product. The crude product was clean by NMR spectroscopy and used directly in further reactions. Mp (ΔH): 86–89° C. (49 J/g); an endothermic transition at 82° C. was present in the first scan only. IR: 1671 s, 1508 w, 1446 s, 1420 w, 1337 w, 1312 m, 1290 w, 1219 s, 1192 s, 1144 s, 1114 m, 1082 m, 975 w, 954 w, 901 w, 891 w, 860 w, 821 w, 788 m, 736 w, 714 w, 693 w, 684 w, 649 w, 597 w, 543 w, 509 w, 457 w, 409 w cm$^{-1}$. $^1$H NMR: δ 7.30 (d, J=4.0 Hz, 3'-H), 7.51 (d, J=4.0 Hz, 4-H), 7.56 (d, J=4.3 Hz, 3-H), 8.02 (dt, J=4.3 Hz, 1.6 Hz, 4'H). $^{19}$F NMR: δ −74.20 (t, J=12 Hz, CF$_3$), −80.76 (m, COCF$_2$O), −82.99 (m, OCF$_2$CF$_2$O), −87.52 (m, OCF$_2$CF$_2$O), −87.97, (m, OCF$_2$C$_3$F$_7$), −126.09 (br m, OCF$_2$C$_2$F$_4$CF$_3$).

Example 6

5-Bromo-5'-perfluoro(2,5-dimethyl-3,6-dioxanonanoyl)-2,2'bithiophene

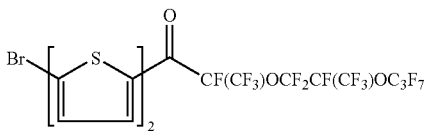

This compound was prepared using an identical procedure to that used in Example 5 to afford 16.1 g (94%) of yellow product. Mp (ΔH):51–55° C. (34 J/g). IR: 1661 s (ν$_{CO}$), 1505 w, 1448 s, 1421 m, 1299 s, 1237 vs, 1203 s, 1149 s, 1081 s, 1029 s, 994 s, 884 m, 835 m, 814 m, 790 s, 752 w, 743 w, 723 m, 705 m, 651 m, 615 m, 532 m, 458 m cm$^{-1}$. $_1$H NMR: δ 7.30 (d, J=3.8 Hz, 3'-H), 7.53 (d, J=4.0 Hz, 4-H), 7.57 (d, J=4,4 Hz, 3-H), 8.15 ('t', J=4.0 Hz, 4'-H). $^{19}$F NMR: δ −76.7 to −82.1 (m, 4 F, OCF2), −79.4 (s, 3 F, CF$_3$), −81.1 (s, 6 F, CF$_3$), −129.0 (m, 1 F, CF), −129.2 (m, 2 F, CF$_2$CF$_2$CF$_3$), −144.7 (m, 1 F, CF). A number of the resonances in the $^{19}$F data are observed as pairs due to the two asymmetric centers of the fluorinated end group. Anal. Calcd for C$_{17}$H$_4$BrF$_{17}$O$_3$S$_2$: C, 28.23; H, 0.56; S, 8.87. Found: 28.6; H, 1.1; 9.1.

Example 7

2-Bromo-5-perfluoro(3,6-dioxadecanoyl)-thiophene

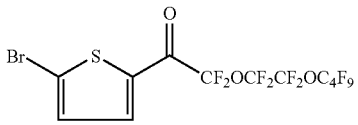

BuLi (3.7 mL, 9.3 mmol) was charged drop wise to a cold (−70° C.) mixture of THF (40 mL) and 2,5-dibromothiophene (1.0 mL, 8.9 mmol). After 40 min at −70° C., C$_4$F$_9$OC$_2$F$_4$OCF$_2$CO$_2$Me (4.1 g, 8.9 mmol) and BF$_3$OEt$_2$ (1.3 mL, 10.3 mmol) were added successively turning the clear, colorless mixture light yellow. After stirring overnight, the volatile materials were removed under reduced pressure.

The remaining liquid was extracted with 100 mL ether, washed with 2×100 mL brine, dried with MgSO$_4$, and stripped to a clear orange liquid. Purification by column chromatography on silica gel afforded a yellow liquid that was dried under vacuum to afford 3.80 g (73%). A larger scale preparation (71 g theoretical yield) afforded 37.8 g (53%) of clean product after it was purified by distillation (bp 55–56° C., 0.1 mm Torr); a precut of 7.7 g collected from 50–55° C. that was approximately 63% product/37% C$_4$H$_3$SCOR$_f$; a 1.1 g post cut was 91% product and 9% C$_4$HBr$_2$SCOR$_f$. IR (neat, KBr plates): 1701 cm−1 (s, ν$_{CO}$). $^1$H NMR: δ 7.52 (d, J=4.4 Hz, 3-H), 7.91 (dt, J=4.4, 1.4 Hz, 4-H). $^{19}$F NMR: δ −74.79 (m, CF$_3$), −80.87 (m, COCF$_2$O), −83.07 (m, OCF$_2$CF$_2$O), −87.61 (m, OCF$_2$CF$_2$O), −88.05 (m, OCF$_2$C$_3$F$_7$), −126.1 (m, CF$_2$CF$_2$CF$_2$CF$_3$).

Example 8

2-Perfluoro(3,6-dioxadecanoyl)-thiophene

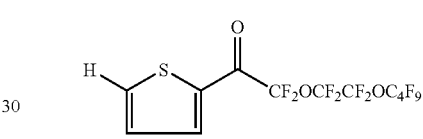

BuLi (7.8 mL, 12.5 mmol) was added to a cold (−65° C.) mixture of THF (50 mL) and thiophene (1.0 mL, 12.5 mmol. The clear, colorless solution was warmed to room temperature, cooled to −65° C., and C$_4$F$_9$OC$_2$F$_4$OCF$_2$CO$_2$Me (5.84 g, 12.7 mmol) and BF$_3$(OEt$_2$) (1.9 mL, 15 mmol) added successively. The yellow solution was stirred cold for 2 hr and then mixed with 2 mL of saturated NH$_4$Cl (aq). The volatile material was removed under reduced pressure, and the residue extracted with 50 mL hexanes.

The solution was filtered, dried with MgSO$_4$, filtered again, and stripped to afford 5.53 g (86%) of clear orange liquid that was clean by NMR spectroscopy. IR: 1700 cm$^{-1}$ (s, ν$_{CO}$). $^1$H NMR: δ 7.41 (dd, J=6.0 Hz, 4.0 Hz, 5-H), 8.08 (m, 3-H), 8.33 (dd, J=4.9 Hz, 1.1 Hz, 4-H). $^{19}$F NMR: δ −74.93 (m, CF$_3$), −80.91 (m, COCF$_2$O), −83.12 (m, OCF$_2$CF$_2$O), −87.67 (m, OCF$_2$CF$_2$O), −88.11 (m, OCF$_2$C$_3$F$_7$), −126.18 (m, CF$_2$CF$_2$CF$_2$CF$_3$).

Example 9

5-Perfluoro(3,6,9-trioxadecanoyl)-2,2':5',2''-terthiophene

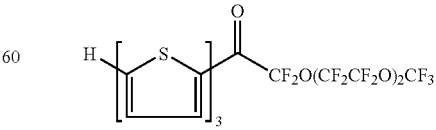

Under nitrogen, a vessel was loaded with 2,2':5',2''-terthiophene (878 mg, 3.53 mmol) and anhydrous THF (75 mL). The solution was cooled at −78° C. and ″BuLi (2.2 mL, 3.5 mmol) was added gradually by syringe. The mixture was stirred cold for 30 min, and then methyl 3,6,9-trioxadecanoate (1.0 mL, 3.8 mmol, 1.1 eq) and BF$_3$OEt$_2$ (0.54 mL, 4.3 mmol, 1.2 eq) were successively added. After another 90 min at −78° C., sat NH4Cl (aq) (20 mL) was added and the mixture was warmed to ambient temperature and further diluted with ether (100 mL) and water (50 mL). The aq phase was separated, and the yellow-green organic phase was washed with 2×100 mL of brine, dried with MgSO$_4$, and filtered.

Analysis by TLC (SiO$_2$ on glass) with 5% EtOAc/balance hexanes showed the main reaction product with $R_f$=0.45. The organic solution was concentrated, adsorbed onto silica gel, and purified by column chromatography (silica gel/hexanes, 1.25 in×10 in) using hexanes eluent to afford 1.03 g (45%) of bright orange product. $^1$H NMR: δ 7.15 (dd, J=5.2 Hz, 3.6 Hz), 7.37 (d, J=4.0 Hz), 7.44 (dd, J=3.6 Hz, 1.2 Hz), 7.55 (dd, J=5.2 Hz, 1.2 Hz), 7.59 (d, J=4.0 Hz), 7.65 (d, J=4.0 Hz), 8.02 (dt, $^3J_{HH}$=4.0 Hz, $^5J_{HF}$=1.6 Hz). $^{19}$F NMR: δ −54.9 (t, J=9.4 Hz, CF$_3$), −74.3 (m, COCF$_2$), −87.4 (m, CF$_2$), −88.1 (br, 2 CF$_2$-groups), −90.1 (q, J=9.4 Hz, CF$_2$OCF$_3$).

Example 10

Synthesis of 5,5'''-bis[perfluoro(3,6-dioxadecanoyl)]-2,2':5',2":5",2'''-quaterthiophene.

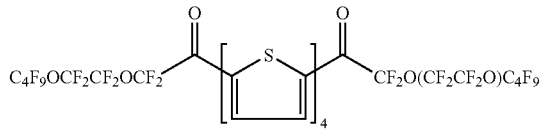

Under a nitrogen atmosphere, a vessel was successively charged with 2-bromo-5-perfluoro(3,6-dioxadecanoyl) thiophene (3.24 g, 5.48 mmol), dry DMF (30 mL), 5,5'-bis(tri-n-butylstannyl)-2,2'-bithiophene (2.04 g, 2.74 mmol), and Pd(PPh$_3$)$_4$ (63 mg, 0.055 mmol). The mixture was bubbled through with nitrogen for 20 min, and then stirred at 85° C. overnight. The reaction mixture was transferred into a mixture of EtOAc (100 mL) and CH$_2$Cl$_2$ (100 mL), stirred, and then poured through a 10–20 μm glass filter frit to isolate the product. The red solid was washed on the frit with methanol (100 mL) and air-dried overnight to afford 2.28 g (70%).

Material used in OTFTs was sublimed at least 2 times. In a typical experiment, 1.01 g was loaded into a train sublimation system. With P=3×10$^{-6}$ Torr, the source zone was ramped to 240° C., with the product zone at 180° C. The product was melted in the source at this point, but not mobile. The source and product zones were ramped to 280° C. and 220° C., respectively, and the sublimation was done in 30 min. Only a negligible film remained at the source. From the product zone was isolated 884 mg (87% of input). TGA: 1% wt loss at 271° C.; 5% wt loss at 285° C.; no residue at 988° C. DSC (20° C./min): 185° C. (−71 J/g), reversible melting point. MALDI-TOF mass spectrometry showed a molecular ion isotopic cluster that contained an abundant peak at m/z1186 1200 (M$^+$), and peaks at M+1 (76%), M+2 (55%), M+3 (22%), and M+4 (8%).

Example 11

Synthesis of 5,5''''-bis[perfluoro(3,6,9-trioxadecanoyl)]-2,2':5',2":5",2''':5''',2''''-quinquethiophene.

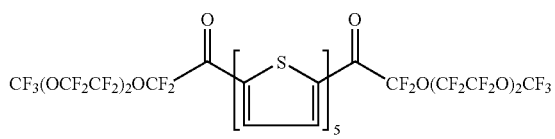

Under nitrogen, a vessel was charged with Pd(PPh$_3$)$_4$ (65 mg, 0.056 mmol, 0.5 mol % per coupling site), 5-Bromo-5'-perfluoro(3,6,9-trioxadecanoyl)-2,2'-bithiophene (3.54 g, 5.54 mmol), DMF (40 mL), and 5,5'-bis(tri-n-butylstannyl) thiophene (1.83 g, 2.76 mmol). The mixture was bubbled through with nitrogen for 20 min, and then stirred at 90° C. for 20 h. The red mixture was cooled to room temperature and the solid was collected on a 10–20 μm filter frit, washed with 2×60 mL isopropanol, and air-dried overnight to afford 2.34 g (71%) of crude, burgundy product.

The material was train sublimed at P=4×10$^{-6}$ Torr with a source temperature of 315° C. (material is melted) and the product collection zone at 180° C. to afford 2.23 g (67%) of red-purple product. The product was sublimed an additional time before device preparation. $^1$H NMR (600 MHz, d$_4$-o-dichlorobenzene, 100° C.): Due to the high temperature used during the data collection (the material has very low solubility), broad, singlets were observed for each of the 5 chemically inequivalent protons; δ 7.79, 7.16, 7.10, 7.06, 7.04. $^{19}$F NMR (564 MHz, d$_4$-o-dichlorobenzene, 100° C.): Data was identical to that reported in preparative examples 1 and 4. MALDI-TOF mass spectrometry showed a molecular ion isotopic cluster that contained an abundant peak at m/z 1200 (M$^+$), and peaks at M+1 (65%), M+2 (45%), M+3 (20%), and M+4 (10%).

Example 12

Synthesis of 5,5''''''-bis[perfluoro(2,5-dimethyl-3,6-dioxanonanoyl)]-2,2':5',2":5",2''':5''',2'''':5'''',2'''''-sexithiophene.

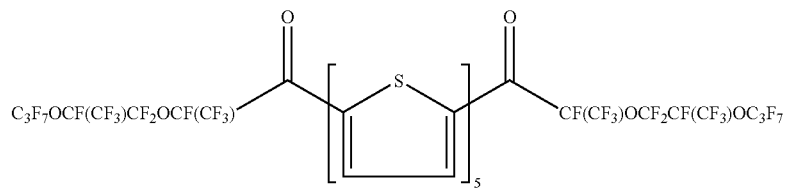

Under a nitrogen atmosphere, a vessel was successively charged with 5-bromo-5'-perfluoro(2,5-dimethyl-3,6-dioxanonanoyl)-2,2'-bithiophene (3.49 g, 4.83 mmol), dry DMF (75 mL), 5,5'-bis(tri-n-butylstannyl)-2,2'-bithiophene (1.80 g, 2.42 mmol), and Pd(PPh$_3$)$_4$ (30 mg, 0.026 mmol). The mixture was bubbled through with nitrogen for 30 min, and then stirred at 100° C. for 5 h. A red ppt formed in the mixture. The solution was cooled to room temperature, and then further with an ice water bath. The solution was poured through a 10–20 gm glass filter frit, and the red solid was washed with methanol (100 mL), hexanes (100 mL), and then air-dried overnight. Yield: 2.79 g, 80%. Material used in OTFTs was sublimed at least 2 times.

In one experiment, 994 mg of material was loaded into a train sublimation system and sublimed with P=2×10$^{-6}$ Torr, source temperature 320° C., and product zone at 240° C. The material melted at the source before volatilizing and moving to the product zone. Isolated 918 mg (92% of input).

IR spectroscopy (KBr pellet, $v_{CO}$=1663 cm–1), combustion analysis, and high resolution mass spectroscopy were consistent with the proposed structure. $^1$H NMR (400 MHz, d6-acetone, internal TMS ref to 0 pm): δ 8.18 (m, 1 H), 7.71 (d, J=4 Hz, 1 H), 7.62 (d,J=4 Hz, 1 H), 7.44 ('d', J=4Hz, 2H),7.38 (d, J=4Hz, 1 H). TGA: 1% wt loss at 365° C.; 5% wt loss at 381° C.; no residue at 988° C. DSC (20° C./min): 150° C. (−17 J/g), 218° C. (−2 J/g), reversible melting point. $^{19}$F NMR data was virtually identical to that in preparative examples 3 and 6. A number of the resonances in the $^{19}$F data are observed as pairs due to the two asymmetric centers of the fluorinated end group. IR (KBr): 1663 s ($v_{CO}$), 1436 s, 1236 vs, 1202 s, 1151 s, 1079 m, 1029 m, 994 s, 981 m, 790 m cm$^{-1}$.

High performance liquid chromatography (HPLC) with a THF solution of the product was carried out using an Agilent Model LC/MSD quadrupole mass spectrometer equipped with an atmospheric pressure chemical ionization (APCI) source. The sample solution was injected into a mobile phase of THF/water (1:1) and data were collected over the mass range of 1,000–2,000 Daltons at a scan rate of approximately 2 scans/second. The only significant ions in the spectrum were seen a m/z 1451, m/z 1452, and m/z 1453, corresponding to a compound having a molecular eight of 1,450, consistent with the proposed product.

Example 13

Fabrication and Testing of OTFTs.

OTFTs were fabricated on doped silicon <100> wafers obtained from Silicon Valley Microelectronics (San Jose, Calif.) with 5 kÅ aluminum on the backside and 1.5 kÅ of sputtered Al$_2$O$_3$ on the front. A 0.1 wt % solution of poly(α-methylstyrene) (average M$_w$ ca 100,300 by GPC) was applied to the surface from toluene by spin coating (500 rpm for 20 s, followed by 2000 rpm for 40 s). Samples were placed in a 110° C. oven and baked for 30 min after spin coating. The resultant polymer layer was about 100 Å, as measured by single beam ellipsometry. Thin films (~600 Å) of the perfluoroacyl thiophenes described above were deposited by physical vapor deposition at a pressure ≦5×10$^{-6}$ Torr. Samples were then moved to another vacuum chamber where gold source-drain contacts (600 Å) were evaporated on to the organic film through a polymeric shadow mask.

Figure 2:
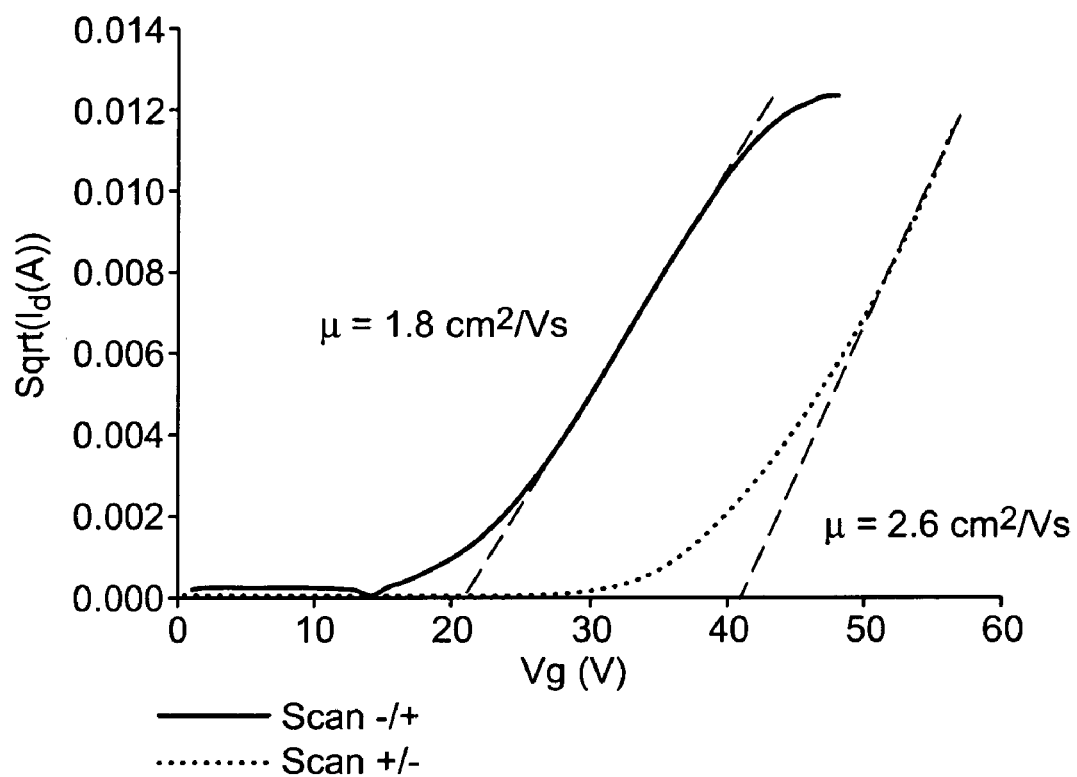
FIG. 2 is a graph of the performance of a semiconductor device of using the oligothiophene semiconductor of Example 10.

FIG. 2 shows characterization data ($I_D^{1/2}$ vs V$_G$ curves calculated from $I_D$–V$_G$ transfer curves) for thin film transistors made using 5,5'''-bis[perfluoro(3,6-dioxadecanoyl)]-2,2':5',2'':5'',2'''-quaterthiophene (Example 10) in the semiconductor layer. The data is in the saturated regime, with drain voltages (V$_D$) equal to the maximum gate voltage (V$_G$) in each case. The devices were measured under 10$^{-6}$ torr vacuum. Data is plotted for both negative-to-positive (−/+) and positive-to-negative (+/−) scans of the gate voltage. The saturation electron mobility (μ$_e$) was calculated from the slope of the $I_D^{1/2}$ vs V$_G$ trace at the points indicated using standard metal-oxide-semiconductor field-effect transistor (MOSFET) equations (See Sze, S. M. *Physics of Semiconductor Devices;* 2nd ed.; John Wiley & Sons: New York, 1981). For the device shown in FIG. 2, the mobility was 1.8 cm$^2$/Vs for a negative-to-positive V$_G$ scan, and 2.6 cm$^2$/Vs for a positive-to-negative scan. Additional data for other devices on the same wafer are tabulated in Table 1.

Figure 3:
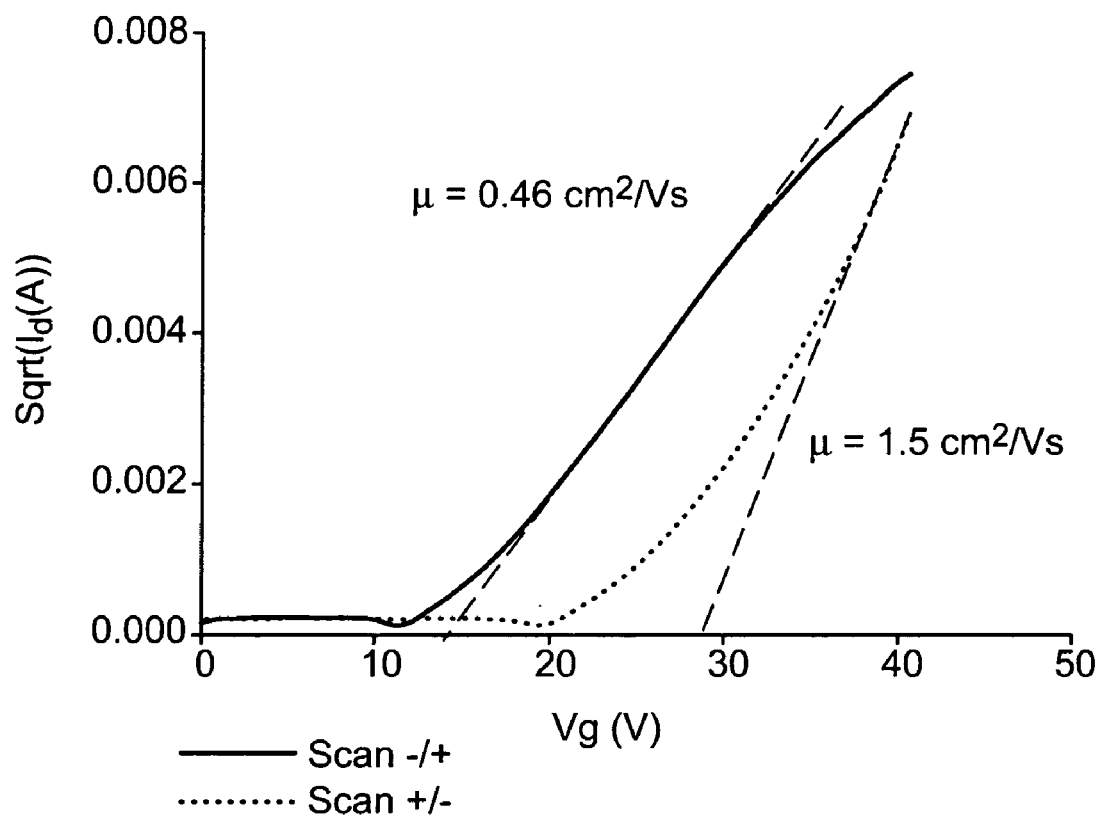
FIG. 3 is a graph of the performance of a semiconductor device using the oligothiophene semiconductor of Example 11.

FIG. 3 shows $I_D^{1/2}$ vs V$_G$ curves for a thin film transistor made using 5,5''''-bis[perfluoro(3,6,9-trioxadecanoyl)]-2,2':5',2'':5'',2''':5''',2''''-quinquethiophene (Example 11) in the semiconductor layer. Devices were fabricated and tested as described above. Table 2 lists additional data for other devices on the same wafer.

With regard to the thin film transistors using the n-channel semiconductor oligothiophene of the invention, the resulting mobility values are the highest values reported to date for n-channel organic semiconductor materials, and are comparable in performance to p-channel semiconductors such as pentacene.

TABLE 1

Additional data for devices made with 5,5'''-bis[perfluoro(3,6-dioxadecanoyl)]-2,2':5',2'':5'',2'''-quaterthiophene (Example 10)

| Test # and scan direction | | n-channel mobility (cm$^2$/Vs) |
|---|---|---|
| 1 | −/+ | 1.3 |
|   | +/− | not measured |
| 2 | −/+ | not measured |
|   | +/− | 1.7 |
| 3 | −/+ | not measured |
|   | +/− | 1.6 |
| 4 | −/+ | 1.6 |
|   | +/− | not measured |
| 5 | −/+ | 1.7 |
|   | +/− | not measured |
| 6 | −/+ | 1.7 |
|   | +/− | not measured |
| 7 | −/+ | 1.7 |
|   | +/− | 1.8 |
| 8 | −/+ | 1.6 |
|   | +/− | not measured |

TABLE 2

Additional data for devices made using 5,5''''-bis[perfluoro(3,6,9-trioxadecanoyl)]-2,2':5',2'':5'',2''':5''',2''''-quinquethiophene (Example 11)

| Test # and scan direction | | n-channel mobility (cm$^2$/Vs) |
|---|---|---|
| 1 | −/+ | 0.47 |
|   | +/− | 0.89 |
| 2 | −/+ | 0.34 |
|   | +/− | 1.1 |
| 3 | −/+ | 0.40 |
|   | +/− | 1.7 |
| 4 | −/+ | 0.40 |
|   | +/− | 1.1 |
| 5 | −/+ | 0.46 |
|   | +/− | 1.1 |

We claim:

1. A compound of the formula:

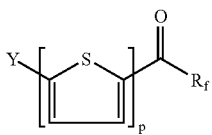

wherein Y is a hydrogen atom, a halogen atom, an alkyl group, and aryl group or a perfluoroether acyl group, p is at least one, and $R_f$ is a perfluoroether group.

2. The compounds of claim 1 of the formula:

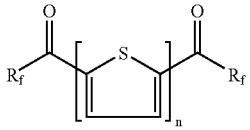

wherein each $R_f$ is independently a perfluoroether group, and n is at least 1.

3. The compounds of claim 2 wherein each $R_f$ is a perfluoroalkoxyalkylene group or a perfluoropolyether group.

4. The compounds of claim 2 wherein each $R_f$ corresponds to the formula:

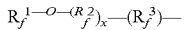

wherein $R_f^1$ represents a perfluoroalkyl group, $R_f^2$ represents a perfluorinated polyalkyleneoxy group consisting of perfluoroalkyleneoxy groups having 1 to 4 perfluorinated carbon atoms or a mixture of such perfluoroalkyleneoxy groups, $R_f^3$ represents a perfluoroalkylene group, x is 0 to 25.

5. The compounds of claim 4 wherein each $R_f^2$ is independently selected from selected from —$CF_2$—$CF_2$—O—, —CF($CF_3$)—$CF_2$—O—, —$CF_2$—CF($CF_3$)—O—, —$CF_2$—$CF_2$—$CF_2$—O—, —$CF_2$—O—, —CF($CF_3$)—O—, and —$CF_2$—$CF_2$—$CF_2$—$CF_2$—O—.

6. The compounds of claim 4 wherein each $R_f^3$ is independently selected from —$CF_2$—$CF_2$—, —CF($CF_3$)—$CF_2$—, —$CF_2$—CF($CF_3$)—, —$CF_2$—$CF_2$—$CF_2$—, —$CF_2$—O—, —CF($CF_3$)—, and —$CF_2$—$CF_2$—$CF_2$—$CF_2$—.

7. The compounds of claim 4 wherein x is 1 to 4.

8. The compounds of claim 2 wherein each $R_f$ is $R_f^1$—O—[CF($CF_3$)—$CF_2$O]$_x$—CF($CF_3$)— wherein $R_f^1$ is a perfluoroalkyl group and x is at least one.

9. The compounds of claim 4 wherein $R_f^1$ represents a perfluorinated alkyl group having 1 to 6 carbon atoms.

10. The compounds of claim 2 wherein n is 3 to 6.

11. The compounds of claim 2 wherein $R_f$ is

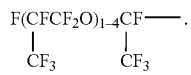

12. A method of preparing a compound of claim 2 comprising:
reacting a bis-trialkylstannyl (oligo)thiophene with a 2-halo-5-perfluoroetheracyl thiophene or a 5-halo-5'-perfluoroetheracyl oligothiophene in the presence of a palladium catalyst.

13. The method of claim 12 comprising the steps of:
reacting a bis-trialkylstannyl thiophene of the formula:

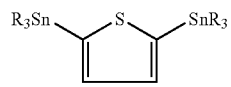

wherein each R is selected from a lower alkyl group, with a 2-halo-5-perfluoroetheracylthiophene of the formula:

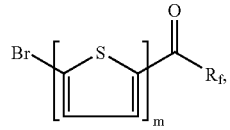

where m is 1 to 3, and $R_f$ is a perfluoroether group, in the presence of a palladium catalyst.

14. The method of claim 13 wherein the compound of the formula:

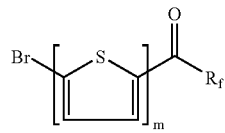

is prepared by brominating a compound of the formula:

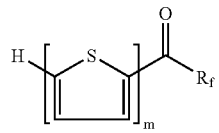

each m is 2 to 3, and $R_f$ is a perfluoroether group.

15. The method of claim 14 where the compound of the formula:

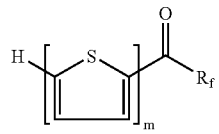

is prepared by treating of the oligothiophene compound of the formula:

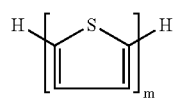

with an alkyl lithium compound, followed by quenching the thienyl anion with a perfluorinated ether ester of the formula
$R_f$—CO—OR, where $R_f$ is a perfluorinated ether group and R is an alkyl group, in the presence a Lewis acid catalyst, where m is 1 to 3.

16. The method of claim 15, where the Lewis acid catalyst is a boron trifluoride etherate.

17. The method of claim 14 where the compound of the formula:
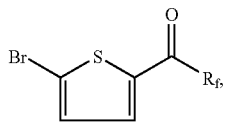
is prepared by treating of the 2,5-dihalothiophene with an alkyl lithium compound, followed by quenching the thienyl anion with a perfluorinated ether ester of the formula $R_f$—CO—OR, where $R_f$ is a perfluorinated ether group and R is an alkyl group, in the presence a Lewis acid catalyst, where m is 1 to 3.
* * * * *

UNITED STATES PATENT AND TRADEMARK OFFICE
CERTIFICATE OF CORRECTION

| | |
|---|---|
| PATENT NO. | : 7,211,679 B2 |
| APPLICATION NO. | : 11/076268 |
| DATED | : May 1, 2007 |
| INVENTOR(S) | : Christopher P. Gerlach |

It is certified that error appears in the above-identified patent and that said Letters Patent is hereby corrected as shown below:

Title Page, item (57)
Abstract
Delete "α,ω-bis(2- perfluoroether" and insert in place thereof
-- α,ω-bis-2- perfluoroether --.

Title Page, item (56) References Cited (continued)
Page 2, Column 1
U.S. Patent Documents, Line 8, delete "6,127,496" and insert in place thereof
-- 6,127,498 --.

Other Publications, Line 3, delete "Flourinated" and insert in place thereof
-- "Fluorinated --.

Page 2, Column 2
Other Publications, Line 12, delete "(2004)" and insert in place thereof -- (2000), --.

Other Publications, Line 15, delete "Perfluoroalky-versus" and insert in place thereof
-- Perfluoroalkyl-versus --.

Other Publications, Line 24, delete "Spectroschopy," and insert in place thereof
-- Spectroscopy, --.

Column 1
Line 51, after "electrode" insert -- . --.

Column 2
Line 16, after "formula" insert -- : --.

Column 4
Line 64 (approx), delete "alkyoxy" and insert in place thereof -- alkyloxy --.

Column 5
Line 15 (approx.), after "formula" insert -- : --.

Column 7
Line 59, delete "α,ω-bis(2- perfluoroether" and insert in place thereof
-- α,ω-bis-2- perfluoroether --.

UNITED STATES PATENT AND TRADEMARK OFFICE
CERTIFICATE OF CORRECTION

PATENT NO. : 7,211,679 B2
APPLICATION NO. : 11/076268
DATED : May 1, 2007
INVENTOR(S) : Christopher P. Gerlach It is certified that error appears in the above-identified patent and that said Letters Patent is hereby corrected as shown below:

Column 11
Line 26 (approx.), delete "OTFT ." and insert in place thereof -- OTFT. --.

Line 36 (approx.), delete "terephthal ate)," and insert in place thereof -- terephthalate), --.

Column 12
Line 60, after "al.)" insert -- . --.

Line 62, delete "polynorbomene," and insert in place thereof -- polynorbornene --.

Column 16
Line 64, delete $BF_3.OEt_2$" and insert in place thereof -- $BF_3 \cdot OEt_2$ --.

Column 17
Line 10, delete "(vco)," and insert in place thereof -- ($v_{co}$), --.

Column 18
Line 9, after "F" insert -- . --.

Column 19
Line 26, delete "2,2'bithiophene" and insert in place thereof -- 2,2'-bithiophene --.

Line 42 (approx.), delete "$_1H$" and insert in place thereof -- $^1H$ --.

Column 20
Line 34, delete "(1.0 mL, 12.5 mmol." and insert in place thereof -- (1.0 mL, 12.5 mmol.) --.

Column 21
Line 5, delete "NH4Cl" and insert in place thereof -- $NH_4Cl$ --.

Column 23
Line 10, delete "gm" and insert in place thereof -- μm --.

Column 24
Line 3, delete "torr" and insert in place thereof -- Torr --.

UNITED STATES PATENT AND TRADEMARK OFFICE
CERTIFICATE OF CORRECTION

PATENT NO. : 7,211,679 B2
APPLICATION NO. : 11/076268
DATED : May 1, 2007
INVENTOR(S) : Christopher P. Gerlach It is certified that error appears in the above-identified patent and that said Letters Patent is hereby corrected as shown below:

Column 25
Line 30, in claim 4, delete " 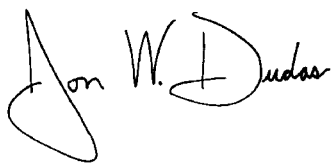 " and insert in place thereof
-- $R_f^1$-O-$(R_f^2)_x$-$R_f^3$)- --.

Column 25
Line 38 (approx.), in claim 5, before "–$CF_2$–$CF_2$–O–," delete "selected from".

Signed and Sealed this

Twentieth Day of May, 2008

JON W. DUDAS
*Director of the United States Patent and Trademark Office*